US010807688B2

(12) United States Patent
Xiao

(10) Patent No.: US 10,807,688 B2
(45) Date of Patent: *Oct. 20, 2020

(54) DIVING MASK SYSTEM

(71) Applicant: Wenzi Xiao, Shenzhen (CN)

(72) Inventor: Wenzi Xiao, Shenzhen (CN)

(\*) Notice: Subject to any disclaimer, the term of this patent is extended or adjusted under 35 U.S.C. 154(b) by 202 days.

This patent is subject to a terminal disclaimer.

(21) Appl. No.: 16/031,090

(22) Filed: Jul. 10, 2018

(65) Prior Publication Data

US 2019/0118917 A1   Apr. 25, 2019

Related U.S. Application Data

(63) Continuation-in-part of application No. 15/832,290, filed on Dec. 5, 2017, which is a continuation-in-part of application No. 15/789,717, filed on Oct. 20, 2017.

(51) Int. Cl.
*B63C 11/16* (2006.01)
*B63C 11/12* (2006.01)
*A61F 9/02* (2006.01)

(52) U.S. Cl.
CPC ............... *B63C 11/16* (2013.01); *A61F 9/027* (2013.01); *B63C 2011/125* (2013.01); *B63C 2011/128* (2013.01)

(58) Field of Classification Search
CPC ............... B63C 11/16; B63C 2011/125; B63C 2011/128; B63C 11/14; B63C 2011/165; B63C 11/18; B63C 11/02; B63C 11/12; B63C 11/00; B63C 2011/186; A61F 9/027; B63B 2730/00
See application file for complete search history.

(56) References Cited

U.S. PATENT DOCUMENTS

| 5,181,506 A | * | 1/1993 | Tardiff, Jr. | A61F 9/02 |
| | | | | 128/201.22 |
| 2016/0297505 A1 | * | 10/2016 | Caprice | B63C 11/16 |
| 2017/0334531 A1 | * | 11/2017 | Shiue | A62B 9/02 |
| 2019/0002068 A1 | * | 1/2019 | Godoy | B63C 11/205 |
| 2019/0118918 A1 | * | 4/2019 | Xiao | B63C 11/16 |

\* cited by examiner

*Primary Examiner* — Timothy A Stanis
*Assistant Examiner* — Arielle Wolff
(74) *Attorney, Agent, or Firm* — Jeffrey G. Degenfelder; Carstens & Cahoon, LLP

(57) ABSTRACT

A diving mask system is disclosed comprising a faceplate having a lateral partition on an interior surface delineating an upper and lower section, the lower section comprising a region that extends away from the upper section and includes at least one cutout section fitted with a complementary-shaped flexible insert that enables a user to grasp the nose. The faceplate further includes a rigid annular support frame either bonded to or extending out from a backside of said flange, the frame being configured within the outer periphery of said flange. A flexible annular sidewall skirt is attached to the support frame. The flexible skirt includes a lateral nose piece section attached to the partition. The lateral nose piece section having an inlet aperture and check valve for inhaled air, and an orifice through which an exhalation conduit having a separate check valve extends from the lower chamber to a snorkel device forming a passageway for exhaled air to pass through the upper chamber to the snorkel device. A quick-release clasp mechanism attached to the mask's elastic retention straps is also disclosed.

28 Claims, 21 Drawing Sheets

DIVING MASK SYSTEM

CROSS-REFERENCE TO RELATED APPLICATION

This application is a continuation-in-part of U.S. patent application Ser. No. 15/832,290, filed on Dec. 5, 2017, which is a continuation-in-part of U.S. patent application Ser. No. 15/789,717, filed on Oct. 20, 2017.

BACKGROUND OF THE INVENTION

1. Technical Field of the Invention

The present invention relates to a diving mask used for snorkeling and scuba diving, and more particularly, to an improved full-face snorkel and scuba diving mask that allows both mouth and nasal breathing.

2. Description of Related Art

Snorkeling allows observation of marine life while swimming on the surface of the water or at moderate depths. When snorkeling, in order to prevent water getting into the eyes, ears and mouth, most divers use a snorkel mask. Snorkeling masks have long been popular for providing a simple and cheap way to see underwater clearly when swimming. Typically, snorkeling masks comprise a face mask for viewing and a snorkel device for breathing. One drawback of conventional snorkeling masks is that they typically offer a limited field of view. Another shortcoming of conventional snorkeling masks is its fixed-shape silicon frame, which is not always suited to the different face contours of different users. When a silicone frame does not match the contours of a diver's face, water leakage often occurs resulting in water entering the interior of the diver's mask, negatively affecting its normal use. Still another drawback of the conventional snorkel device is that the breathing tube fits in the mouth so that the diver can only breathe through the mouth.

More recently, full-face snorkeling masks incorporating a snorkel device and offering improved visibility and the ability to breathe through the nose and mouth have begun to appear in the marketplace. One such example is disclosed in U.S. Publ. 2016/0297505 to Caprice et al. This mask includes a faceplate surrounded by a hollow frame assembly; a flexible skirt mounted on the frame assembly, the flexible skirt having a sealing lip about its inner periphery and comprising a lateral partition delimiting an upper chamber and a lower chamber, the partition being arranged to bear upon the top of a user's nose when the mask is worn by the user so that the user's mouth and nose are positioned within the lower chamber, the partition having at least one passageway arranged to allow circulation of air from the upper chamber to the lower chamber during an inhalation phase; a conduit having an inlet channel enabling entry of ambient air and a first escape channel enabling exit of exhaust air, the conduit being configured on the exterior of the mask's upper and lower chambers and extending at an upper part of the hollow frame assembly, the inlet channel being in fluid communication with the upper chamber, and the first escape channel being in fluid communication with the lower chamber, the hollow frame assembly comprising at least one air duct, the air duct having an upper end opening into the first escape channel, and a lower end opening into the lower chamber.

While an improvement on the prior art snorkel masks, the mask disclosed in the Caprice et al. '505 reference still has a number of deficiencies. For example, the hollow frame assembly configured about the outer periphery of the mask is excessively large and bulky due to its incorporation of a complex system of breathing conduits and a snorkel coupling sleeve. In addition, the flexible skirt comprises a peripheral sealing lip constructed of a single silicone layer that is arranged to bear against the user's face so as to prevent water from entering between the user's face and the faceplate. However, since it is a single layer, the sealing lip is susceptible to not matching the contours of a diver's face causing leakage in the mask. In addition, because the lower portion of the mask disclosed in the Caprice et al. '505 reference is entirely enclosed behind the rigid faceplate, a user is unable to readily pinch his nose to clear his ears (i.e., equalize the pressure between the ears and sinuses) when diving to depths, without having to remove the mask. The inability to perform the Valsalva procedure while wearing the Caprice mask would cause a user to experience pain and discomfort due to water pressure when they are snorkeling in water of any depth.

Therefore, it is an objective of the invention to provide a full-faced snorkel and diving mask to mitigate and/or obviate the aforementioned problems.

SUMMARY OF THE INVENTION

The present invention overcomes many of the aforementioned disadvantages of prior art by providing a full-face snorkeling and diving mask with superior sealing qualities that is more streamlined and efficient. The individual parts of the mask of the present invention are preferably fused together using injection molding techniques to create a unitary mask body. The improved mask includes a faceplate that incorporates a lateral partition on the interior surface that delineates an upper section from a lower section. In one embodiment, a snorkel coupling and passageway is also incorporated into the upper portion of the faceplate. While the upper portion of the faceplate includes a transparent lens section, the lower portion includes a region that extends away from the transparent lens section and features a first cutout having a flexible insert installed therein which allows the user to readily squeeze the nose when necessary to equalized pressure on the eardrums. In one embodiment, the faceplate may also comprise a drainage or purge valve arranged in the lower or breathing chamber to evacuate liquid to outside the mask. Alternatively, in another embodiment, in place of the drainage or purge valve the faceplate may include a second cutout configured below the first cutout and fitted with a flexible tubular insert defining a passageway through the faceplate to the lower or breathing chamber and dimensioned to fit and seal onto the mouthpiece receiver tube of a conventional $2^{nd}$ stage scuba regulator. The faceplate may also incorporate two or more buckle devices for attaching elastic retention straps to the mask.

The faceplate includes a flange that is formed along the entire outer periphery or rim of the faceplate. The flange is used as a bonding surface to mount and bond the faceplate to a rigid annular rib or support frame configured within the outer periphery of the faceplate. The rigid annular frame provides structural support to the faceplate while remaining contained within the circumference of the outer periphery of the faceplate. Preferably, the rigid annular frame is permanently bonded to the flange of the faceplate. Alternatively, the rigid annular rib or frame may be incorporated into the faceplate. In such a case, the rigid annular rib or frame is an integral portion of the flange of the faceplate and extends longitudinally away from the backside of the flange forming a protruding annular lip configured within the outer periphery of the faceplate.

The mask of the present invention further includes a flexible annular sidewall element or skirt that is affixed to the rigid annular frame or the rigid annular frame portion of the faceplate. The flexible annular skirt is hollow and filled with a gas or other cushioning substance so as to seal the mask to the diver's face while providing a comfortable, ergonomic and waterproof interface with the diver's face. The flexible sealing skirt also includes a lateral nose piece section, attached to the partition of the faceplate, which effectively seals off the upper chamber from the lower chamber when the mask is worn. The lateral nose piece section includes a barrier wall section that is attached to the partition. The lateral nose piece is formed or sculpted so as come in sealing contact with the user's face in the nasal region just above the user's nose.

In one embodiment of the mask of the present invention, the barrier wall section of the lateral nose piece section may includes at least one aperture, which allows inhaled air from the snorkel device to travel through the upper chamber to the lower chamber. Each aperture also comprises an outlet check valve device which allows the flow of inhaled air directed through each aperture solely from the upper chamber towards the lower chamber during an inhalation phase by the user. By means of the outlet check valve device, the aperture is closed off during an exhalation phase preventing the flow of exhaled air from rising back into the upper chamber, thereby improving the efficacy of the anti-fogging system of the mask. In a preferred embodiment, the barrier wall section of the lateral nose piece section includes two apertures with matching outlet check valve devices.

In one embodiment of the mask of the present invention, the barrier wall section of the lateral nose piece section may further include at least one orifice through which an exhalation conduit extends from the lower chamber to the snorkel device forming a passageway for exhaled air to pass through the upper chamber to the snorkel device. The passageway allows warm, humid air exhaled by the user to be efficiently exhausted though the snorkel without fogging up the transparent lens of the mask. The lower end of the exhalation conduit may further include an outlet check valve device that permits the flow of exhaled air through each passageway only from the lower chamber through the upper chamber and out through the snorkel device during the exhalation phase. By means of the outlet check valve device, the conduit/passageway is closed off during the inhalation phase preventing the flow of inhaled air from the snorkel device into the lower chamber. In a preferred embodiment, the lateral nose piece section includes two orifices and matching conduits.

Alternatively, in another embodiment of the mask of the present invention, the barrier wall section of the lateral nose piece section does not include any apertures or orifices so that the flow of air between the upper and lower chamber is prevented during use.

In one embodiment of the mask of the present invention, a snorkel device is connected via a snorkel coupling formed in the upper portion of the faceplate. The snorkel device has a ventilation system that provides an air pathway into and out of the mask. In a preferred embodiment, the snorkel device comprises an elongated body which slidably couples to the snorkel coupling on one end and comprises an air-permeable enclosure on the distal end. The elongated body encloses an air passageway which fluidly connects a passageway in the snorkel coupling with the airway inlet near the distal end of the snorkel device.

In a preferred embodiment, the snorkel device provides separate pathways for inhaled and exhaled air. The snorkel device may have a distal end having an air-permeable enclosure. The snorkel device further comprises a shut-off device that is mobile within the enclosure so that when the snorkel is submerged in water the shut-off device is caused to move and close the inlet to the air passageway in the snorkel. Nonetheless, the snorkel device is constructed so that when the user exhales air while under water the inlet may be momentarily forced open to exhaust the air. When the snorkel device is out of the water, the shut-off device does not cover the inlet to the air passageway in the snorkel allowing fresh air be inhaled through the air passageway and into the mask via the upper chamber through the aperture and into the lower chamber.

In a preferred embodiment, the snorkel device is removable from the snorkel coupling formed in the upper portion of the faceplate. With the snorkel device removed, the mask may be quickly and easily converted into a hybrid scuba mask embodiment by connecting a conventional $2^{nd}$ stage scuba regulator to the snorkel coupling using a tubular interface sleeve that is preferably flexible and elastic. One end of the tubular interface sleeve is dimensioned to fit snuggly onto the outer periphery of the snorkel coupling end while the opposing end is dimensioned to fit and seal onto the mouthpiece receiver of a conventional $2^{nd}$ stage regulator. The tubular interface sleeve forms a watertight connection between the conventional $2^{nd}$ stage scuba regulator and the snorkel coupling that fluidly connects the air inlet and exhaust passageways of the mask with the mouthpiece receiver of the regulator.

The scuba-enabled embodiment of the hybrid scuba mask works essentially the same as with a snorkel device attached, however, when a user exhales during the exhalation phase or cycle, the exhaust air travels up and out of the exhaust passageways of the mask and on through the exhaust valve of the conventional $2^{nd}$ stage scuba regulator where it is preferably vented out of an exhaust tee deflector device. Similarly, during an inhalation phase or cycle the user creates a slight vacuum pressure in the air inlet passageways of the mask, which triggers the air supply demand valve of the conventional $2^{nd}$ stage scuba regulator to supply air. The air supplied by the scuba regulator flows through the mouthpiece receiver and into the air inlet passageways of the mask. A wide variety of conventional $2^{nd}$ stage scuba regulators may be used with the scuba-enabled embodiment of the mask.

The flexible hollow skirt, flexible tubular interface and the flexible insert configured in the faceplate are preferably made of silicone while the rigid annular frame and faceplate may be made of rigid plastic such as polypropylene or polycarbonate. The arrangement is advantageous since it allows a mask to be manufactured using a minimum number of parts. Preferably the parts are fused together using injection molding techniques to create a unitary mask body.

The mask of the present invention may also comprise an elastic retention strap which extends between two or more buckle devices incorporated into the faceplate of the mask. In a preferred embodiment, the mask includes two buckle devices extending from the upper portion of the faceplate and two buckle devices extending from the lower portion of the faceplate.

In a preferred embodiment, the elastic retention strap may comprise two elastic retention straps bonded together in the center of both straps. The elastic strap is therefore X-shaped making it possible to cover the rear part of the user's head, thereby providing stability and maintaining the mask on the user's head. A first elastic retention strap having one end attached to a buckle device extending from the upper portion of a first side of the faceplate and a second end attached to a buckle device extending from the lower portion of a first side of the faceplate. A second elastic retention strap having one end attached to a buckle device extending from the upper portion of a second side of the faceplate and a second end attached to a buckle device extending from the lower portion of a second side of the faceplate. This preferred embodiment facilitates the mounting operation of the elastic strap and the holding in place thereof in relation to the mask.

The elastic retention straps may also include a quick-release clasp mechanism for quickly and easily detaching the retention straps from the user's head. In a preferred embodiment, the quick-release clasp mechanism comprises two component parts, which are easily fastened or buckled to one another. In a preferred embodiment, the quick-release clasp mechanism includes a quick-release button, which when pushed quickly unbuckles the two component parts from one another.

BRIEF DESCRIPTION OF THE DRAWINGS

A more complete understanding of the apparatus of the present invention may be had by reference to the following detailed description when taken in conjunction with the accompanying drawings, wherein.

Figure 1:
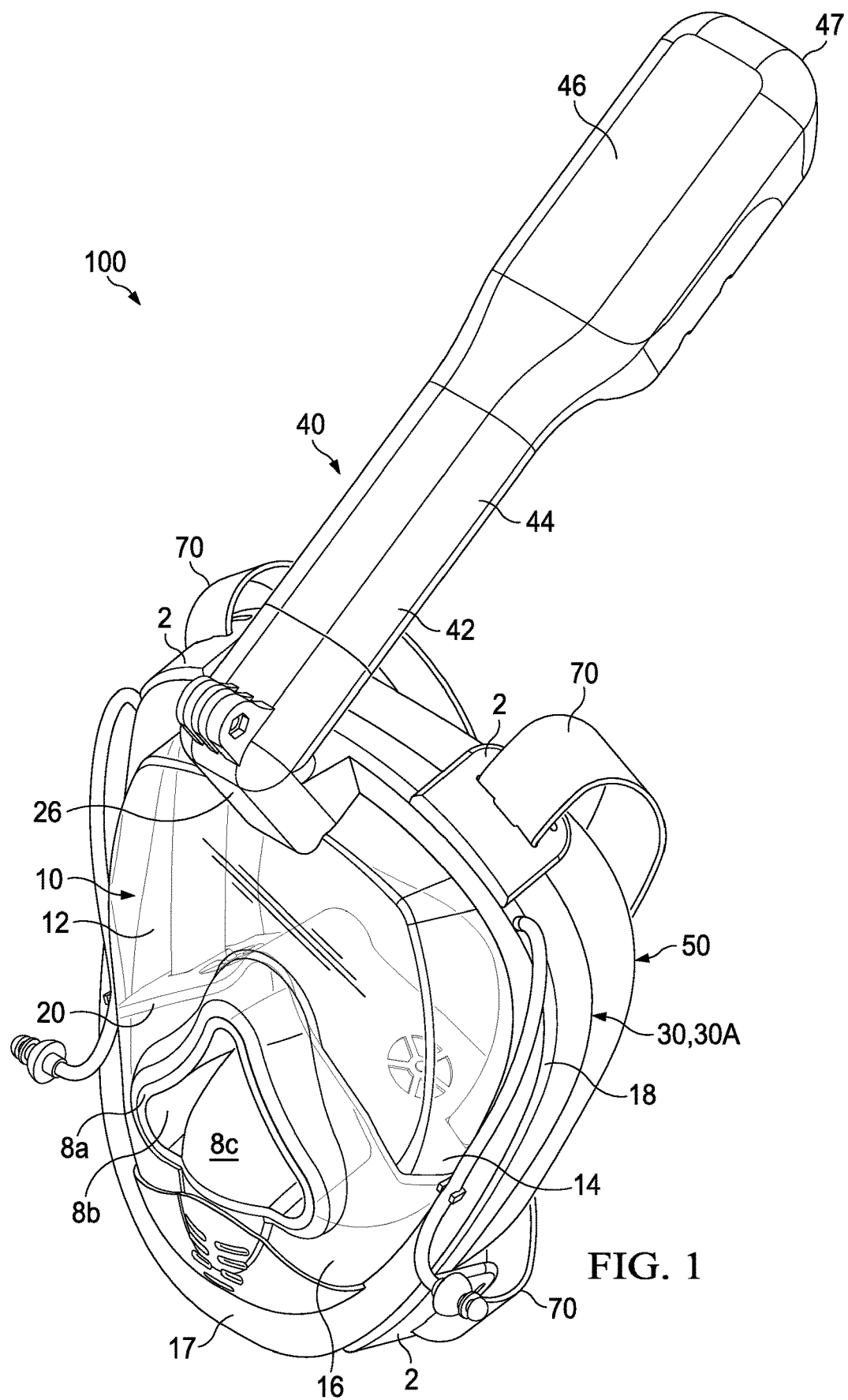
FIG. 1 is a front perspective view of an embodiment of the snorkel and diving mask of the present invention.

Where used in the various figures of the drawing, the same numerals designate the same or similar parts. Furthermore, when the terms "top," "bottom," "first," "second," "upper," "lower," "height," "width," "length," "end," "side," "horizontal," "vertical," and similar terms are used herein, it should be understood that these terms have reference only to the structure shown in the drawing and are utilized only to facilitate describing the invention.

All figures are drawn for ease of explanation of the basic teachings of the present invention only; the extensions of the figures with respect to number, position, relationship, and dimensions of the parts to form the preferred embodiment will be explained or will be within the skill of the art after the following teachings of the present invention have been read and understood. Further, the exact dimensions and dimensional proportions to conform to specific force, weight, strength, and similar requirements will likewise be within the skill of the art, after the following teachings of the present invention have been read and understood.

DETAILED DESCRIPTION OF THE INVENTION

FIG. 1 depicts an example of a first embodiment of a full-faced snorkel mask 100 conforming to embodiments of the present disclosure. With reference now to the Figures, and in particular, FIGS. 1-6, the snorkel mask 100 comprises a faceplate 10 affixed to a rigid annular support rib or frame 30, which in turn is sandwiched between the faceplate 10 and a flexible annular sidewall element or skirt 50.

The faceplate body 10 includes a lateral partition 20 on the interior side of the faceplate 10 that delineates an upper chamber 22 from a lower or breathing chamber 24. As will be understood with reference to FIG. 4, the user's mouth and nose are positioned in the lower chamber 24, whereas the user's eyes are positioned in the upper chamber 22. A snorkel coupling 26 is also incorporated into the upper portion 14 of the faceplate 10. The snorkel coupling 26 includes a passageway 27 that fluidly connects the upper chamber 22 to a snorkel device 40. The upper portion 14 of the faceplate 10 includes a transparent lens section 12, while the lower portion 16 of the faceplate 10 includes a region 5 that extends away from the transparent lens section 12 and includes a first cutout or opening 6 positioned about the user's mouth and nasal region when worn. A flexible waterproof insert 8 is installed in the first cutout opening 6 that allows the user to readily squeeze the user's nose when necessary to equalized pressure on the eardrums. The insert 8 includes an outer peripheral edge or rim 8a that is complementary to the shape and dimension to the first cutout opening 6 in the faceplate 10. The insert 8 is bonded to the cutout opening 6 along the outer peripheral edge or rim 8a with a waterproof seal. The insert may also include thin-walled recessed portions 8b and a thin-walled bulbous nose section 8c, which enables a user's to perform the Valsalva maneuver with their hands by grabbing the nose through the thin-walled bulbous nose section 8c. While the preferred embodiment shown in the Figures comprises a generally triangular shaped first cutout opening 6 and insert 8, it is understood that they could conceivably be of any complementary geometric shape.

The faceplate 10 also incorporates two or more buckle devices 2 for attaching an elastic retention strap 70 to the mask. The faceplate 10 may also comprise a drainage or purge valve 4 configured in the lower portion 16 of the faceplate 10 and arranged to evacuate liquid from the lower or breathing chamber 24 to outside the mask 100. Water contained in the lower chamber 16 can be expelled to outside the mask 100 via the purge valve 4 by means of sharp exhalation.

Figure 3A:
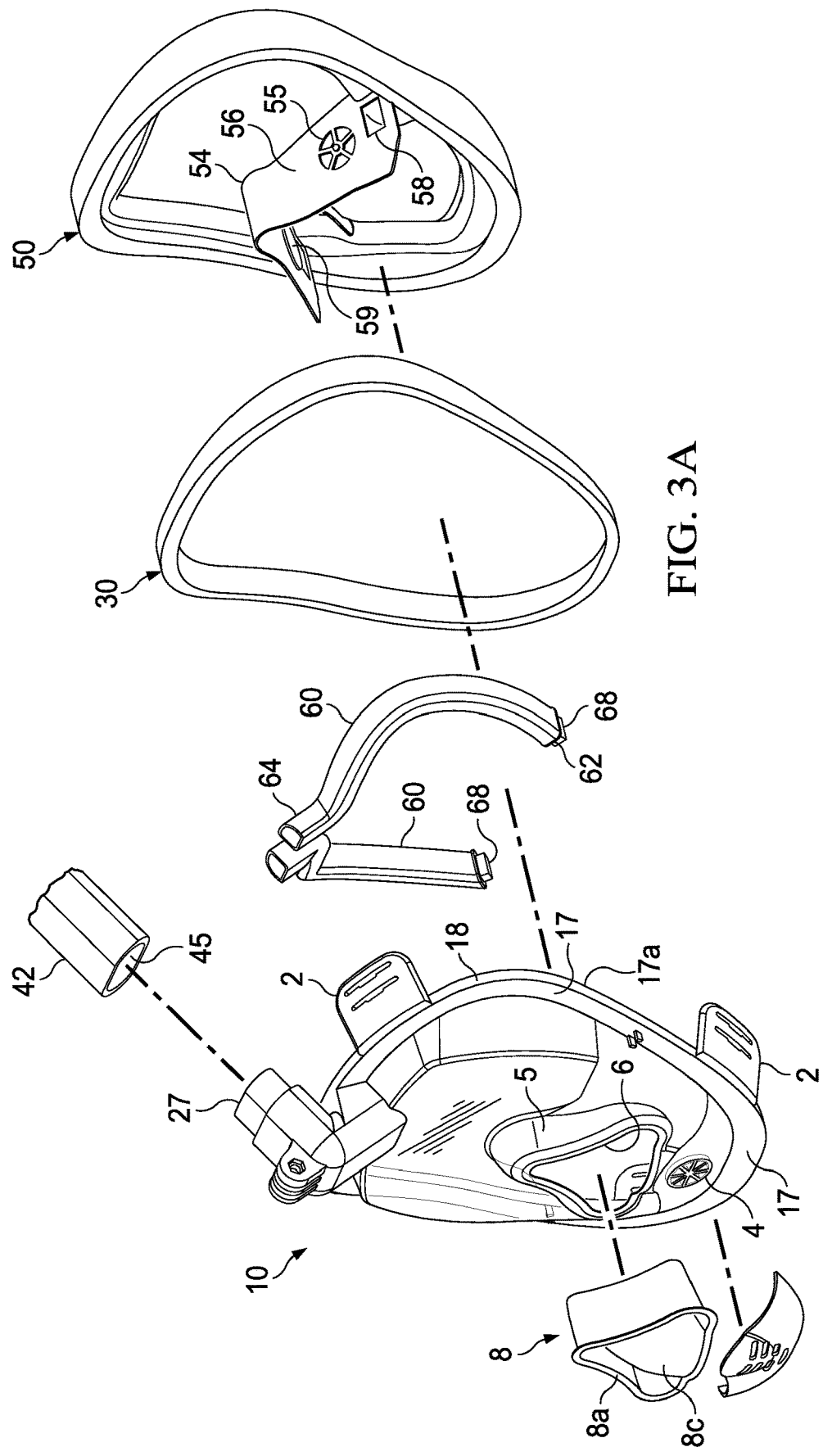
FIG. 3A is an exploded view of a first embodiment of the snorkel and diving mask in FIG. 2.

As shown in FIG. 3A, a flange 17 is formed along the entire outer periphery or rim 18 of the faceplate 10. The flange 17 is used as a bonding surface to affix the faceplate 10 to a rigid annular oblong-shaped support rib or frame 30 configured within the outer periphery 18 of the flange 17 of the faceplate 10. The rigid annular frame 30 is bonded or fused to the back side 17a (i.e., the rearward facing side of the flange 17). The rigid annular frame 30 provides structural support to the faceplate 10 while remaining contained within the circumference of the outer periphery 18 of the faceplate 10. Preferably, the rigid frame 30 is permanently bonded to the outer periphery flange 17 of the faceplate 10.

Figure 3B:
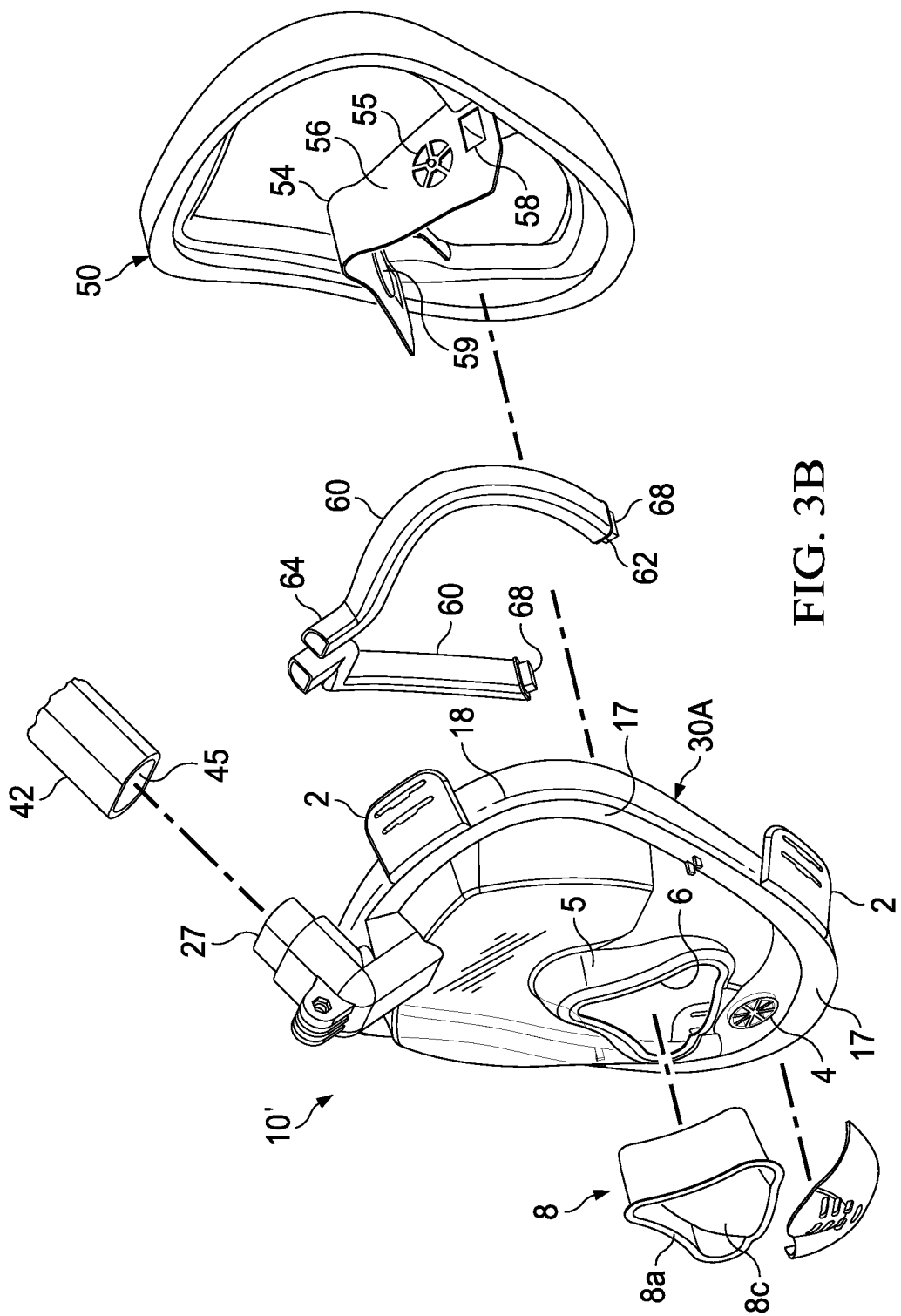
FIG. 3B is an exploded view of a second embodiment of the snorkel and diving mask in FIG. 2.
Figure 4:
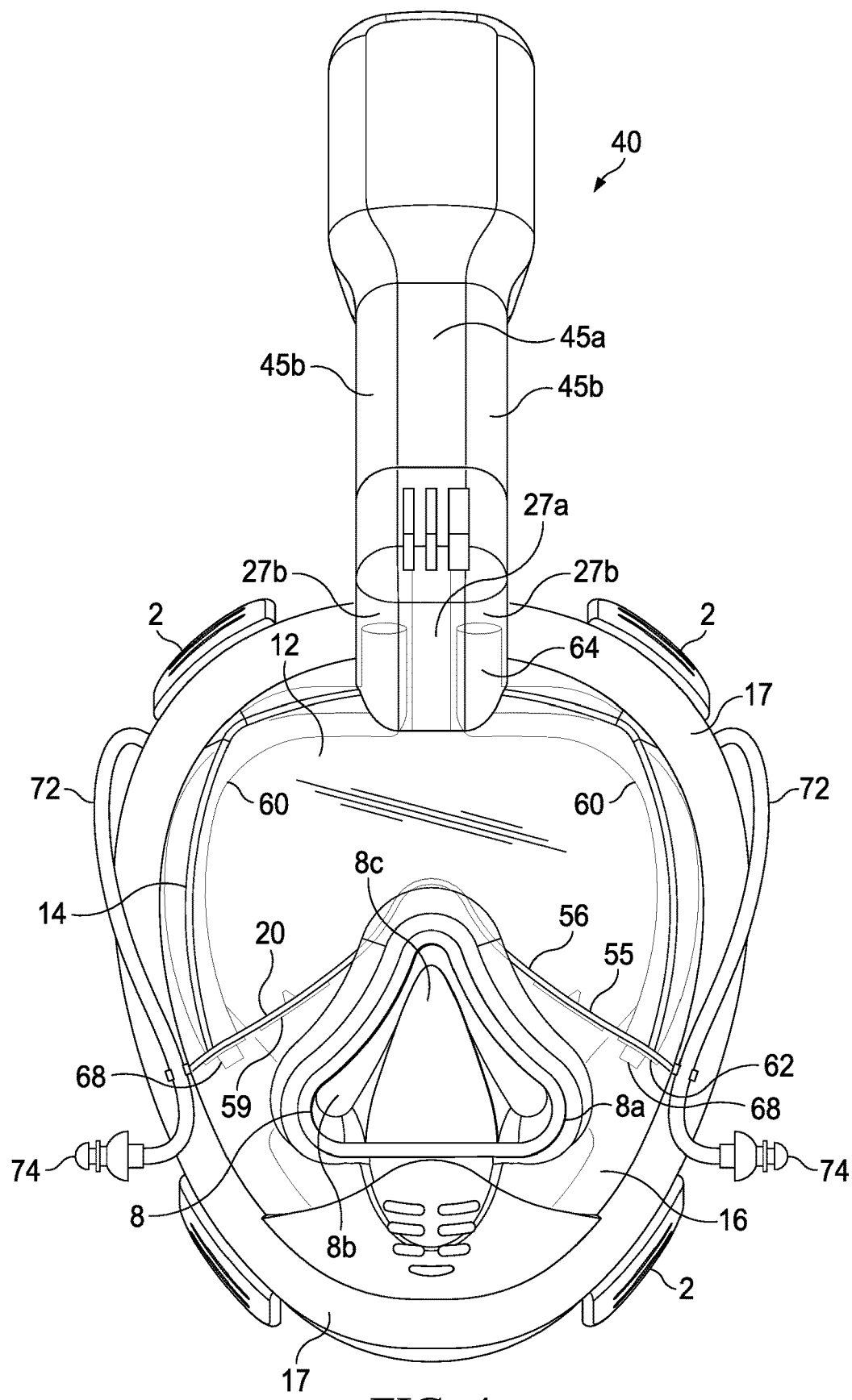
FIG. 4 is a front view of the snorkel and diving mask in FIG. 2.
Figure 5:
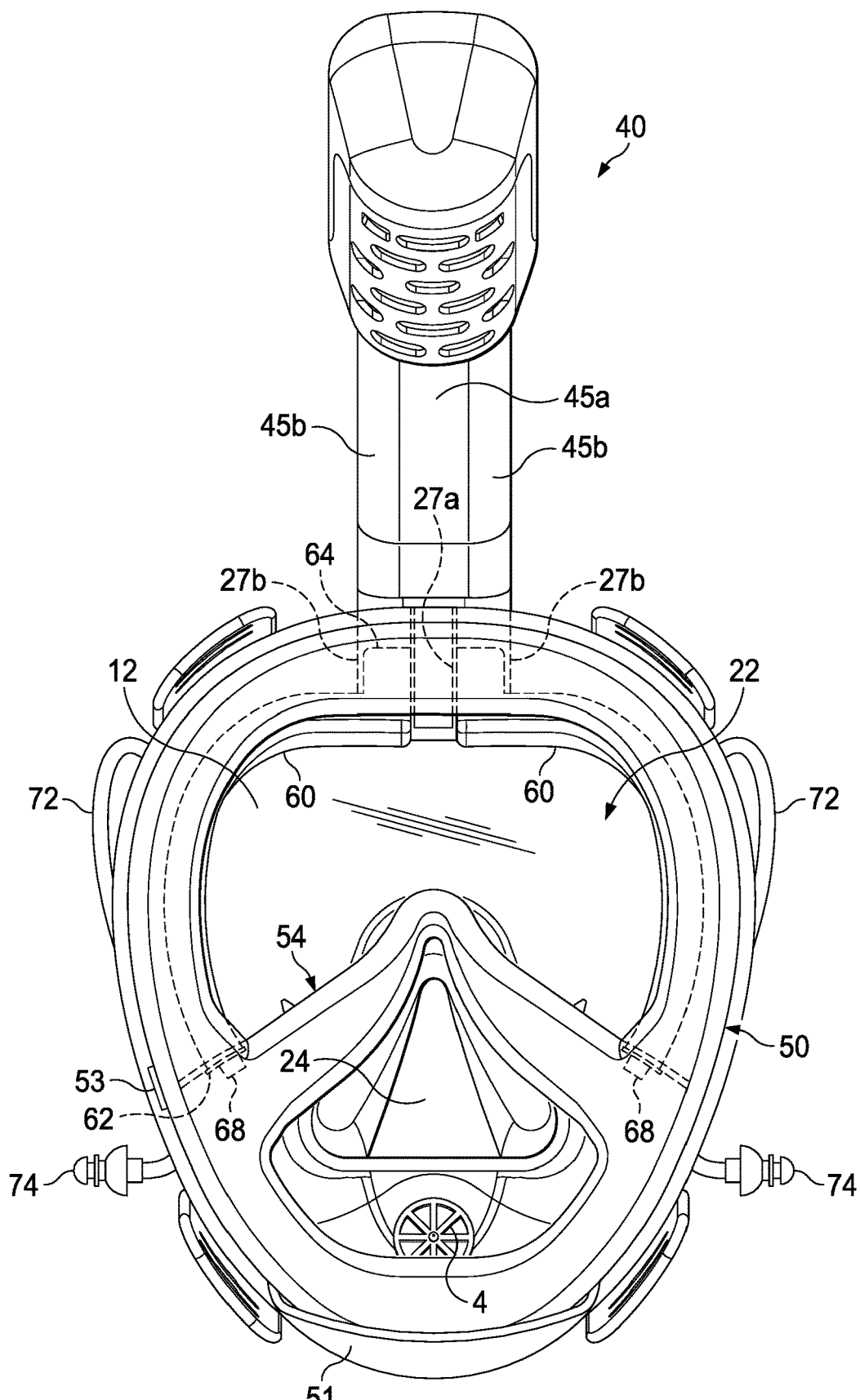
FIG. 5 is a rear view of the snorkel and diving mask in FIG. 2.

With reference now to FIG. 3B, in a preferred embodiment a rigid annular rib or frame is incorporated into the faceplate 10' as an integral extension formed in the flange 17 of the faceplate 10'. The rigid annular rib or frame 30A is formed in the flange 17 and extends longitudinally away from the backside (i.e., the rearward facing side) of the flange 17 forming a protruding annular lip 30A configured within the outer periphery 18 of the faceplate 10'.

With reference again to the Figures, and in particular, FIGS. 1-6, the mask 100 of the present invention further includes a flexible annular sidewall element or skirt 50 that is affixed to the rigid annular frame 30 or the rigid annular lip 30A of the faceplate 10. The flexible annular skirt 50 is hollow and filled with a gas or other cushioning substance so as to seal the mask to the diver's face while providing a comfortable, ergonomic and waterproof interface with the diver's face. Preferably, the flexible annular skirt 50 is filled with air or a gel material. The flexible annular skirt 50 has a generally oblong annular shape having substantially the same circumferential dimensions as faceplate 10 and the annular frame 30.

The flexible sealing skirt 50 also includes a lateral nose piece section 54 attached to the partition 20 of the faceplate 10. The lateral nose piece section 54 effectively seals off at the partition 20 the upper chamber 22 from the lower chamber 24 when the mask 100 is worn. The lateral nose piece section 54 includes a barrier wall section 56 that is preferably flexible, and fixably attached and bonded to the partition 20. The lateral nose piece 54 is formed or sculpted so as come in sealing contact with the user's face in the nasal region just above the user's nose.

The barrier wall section 56 of the lateral nose piece section 54 preferably includes at least one intake aperture 55, which allows air to be inhaled from the snorkel device 40. The inhaled air from the snorkel device 40 enters the mask 100 via the passageway 27 formed the snorkel coupling 26 and travels through the upper chamber 22 to the lower chamber 24 through the intake aperture 55. Each intake aperture 55 in the lateral nose piece section 54 also comprises an inlet check valve device 59 which permits the flow of inhaled air through each intake aperture 55 solely from the upper chamber 22 to the lower chamber 24 during an inhalation phase by the user. By means of the inlet check valve device 59, the intake aperture 55 is sealed during an exhalation phase by the user preventing the flow of exhaled air from rising back into the upper chamber 22, thereby improving the effectiveness of the anti-fogging system of the mask 100. In a preferred embodiment, the barrier wall section 56 of the lateral nose piece section 54 includes two intake apertures 55 and matching inlet check valve devices 59.

The barrier wall section 56 of the lateral nose piece section 54 further includes at least one exhaust orifice 58 through which an exhaust conduit 60 extends from the lower chamber 24 through the upper chamber 22 and to the passageway 27 contained in the snorkel coupling 26 forming an enclosed passageway for exhaled air to pass through the upper chamber 22 to the snorkel device 40. The enclosed passageway 60 allows warm, humid air exhaled by the user to be efficiently exhausted though the snorkel device 40 without fogging up the transparent lens section 12 of the mask 100. As shown in the Figures, and particularly FIG. 4, the exhaust conduit 60 is configured about the inner periphery of the upper chamber 22 adjacent to the flexible annular sidewall element 50. The lower end 62 of the enclosed passageway 60 is sealed within the exhaust orifice 58 of the barrier wall section 56, while the upper end 64 is configured within the passageway 27 of the snorkel coupling 26. The lower end 62 of the exhaust conduit 60 may also include an outlet check valve device 68, which prevents the flow of air through the exhaust conduit 60 during the inhalation phase or cycle. By means of the outlet check valve device 68, the exhaust conduit 60 is sealed during an inhalation phase or cycle by the user preventing flow of inhaled air through the exhaust conduit 60. In a preferred embodiment depicted in the Figures, the barrier wall section 56 of the lateral nose piece section 54 includes two exhaust orifices 58 and matching exhaust conduits/enclosed passageways 60 with an outlet check valve device 68 configured at the lower end.

Figure 2:
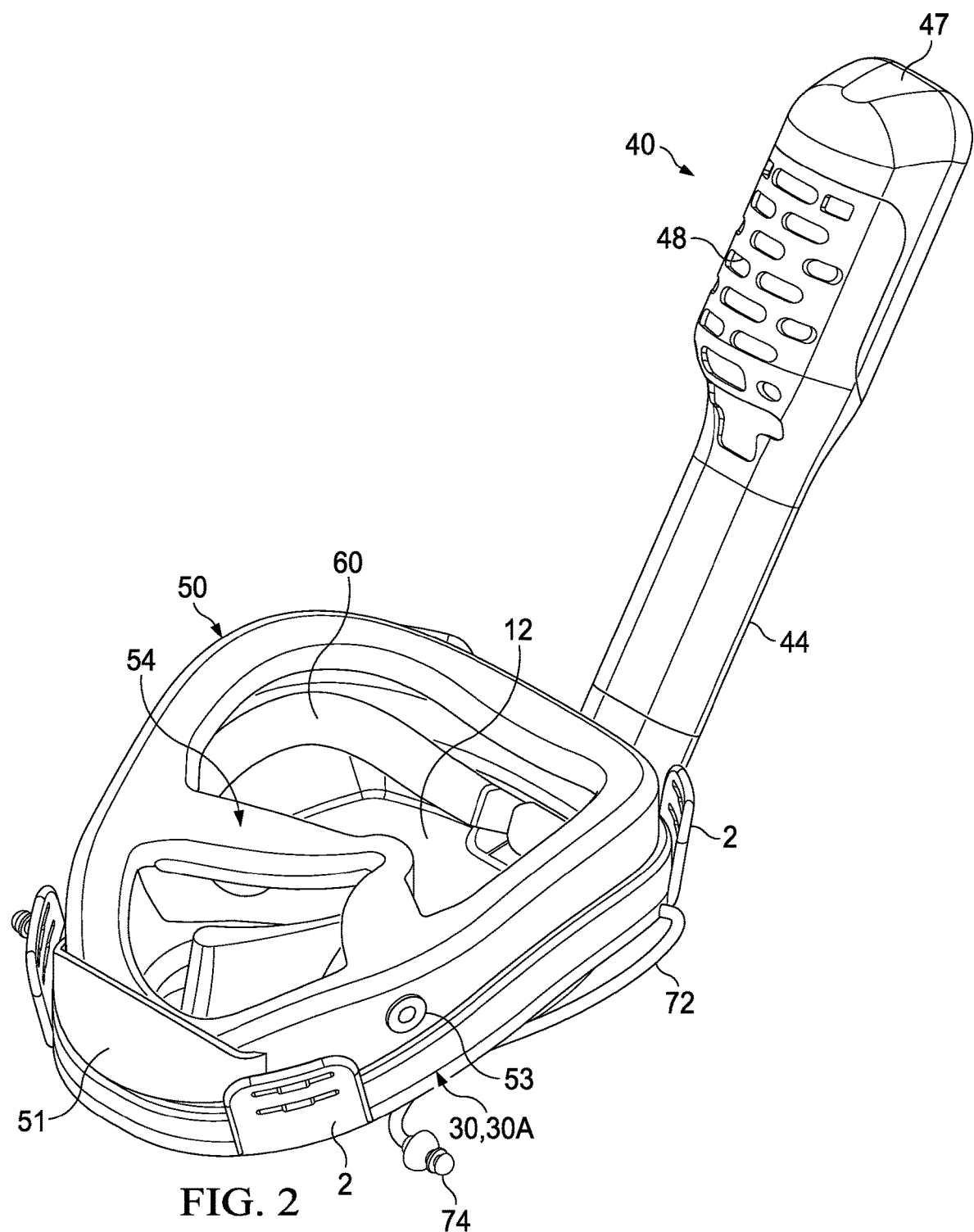
FIG. 2 is a rear perspective view of the snorkel and diving mask in FIG. 1 with the elastic restraining straps removed.
Figure 6:
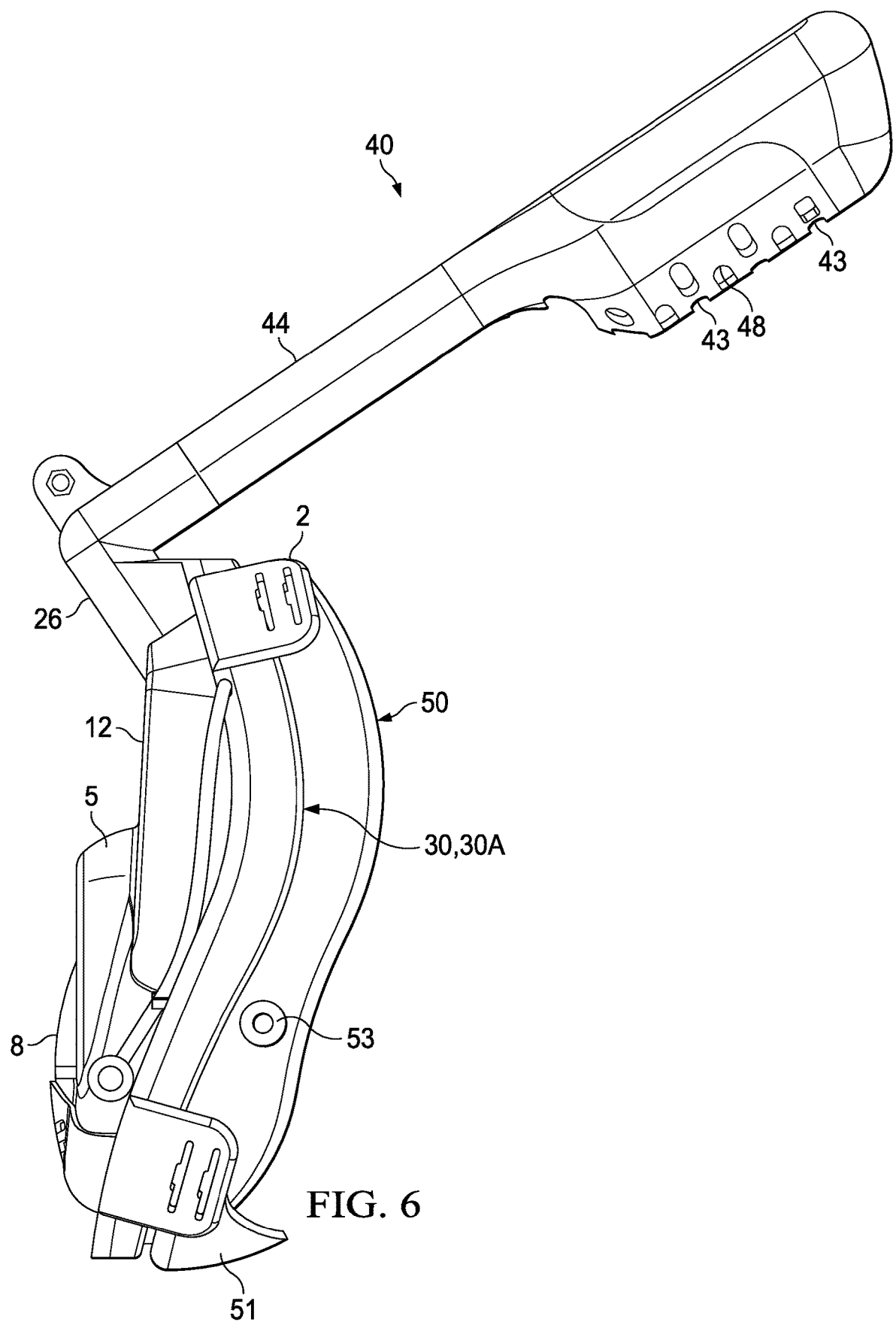
FIG. 6 is a side view of the snorkel and diving mask in FIG. 2.

The flexible annular skirt 50 may also include a valve device 53 for varying the amount of cushioning substance in the hollow annular skirt 50. For example, the valve device 53 could be a simple air valve for increasing or decreasing the amount of air contained in the hollow annular skirt 50. The hollow annular skirt 50 may further include a chin guard 51 configured at the bottom of the mask 100. As depicted in FIGS. 2 and 6, the chin guard 51 extends towards the back of the mask providing protection for the user's chin and assisting in maintaining the proper alignment and positioning of the mask on the user's face.

A snorkel device 40 is connected via the snorkel coupling 26 formed in the upper portion 14 of the faceplate 10. The snorkel device 40 may include a ventilation system that provides an air pathway into and out of the mask 100. In a preferred embodiment, the snorkel device 40 comprises an elongated body 44, which slidably couples to the snorkel coupling 26 on one end 42, and includes an air-permeable enclosure 48 on the distal end. The elongated body 44 encloses an air passageway 45 which fluidly connects a passageway 27 in the snorkel coupling 26 with the airway inlet 43 near the distal end 46 of the snorkel device 40.

The snorkel device 40 may have a distal end 46 having an air-permeable enclosure 48 containing an air inlet 43. The snorkel device 40 may further comprise a shut-off device that is mobile within the enclosure so that when the snorkel device 40 is submerged in water the shut-off device is caused to move and close the inlet to the air passageway 45 in the snorkel device 40. Nonetheless, the snorkel device 40 is constructed so that when a user exhales air while under water the inlet 43 may be momentarily forced open to exhaust the air.

When the snorkel device 40 is out of the water, the shut-off device does not cover the inlet to the air passageway 45 in the snorkel 40 allowing fresh air be inhaled through the air passageway 45 and into the upper chamber 22 of the mask 100, through the intake apertures 55 and past inlet check valve 59 into the lower chamber 24. In a preferred embodiment, the snorkel device 40 is detachable from the snorkel coupling 26 formed in the upper portion 14 of the faceplate 10.

Figure 7B:
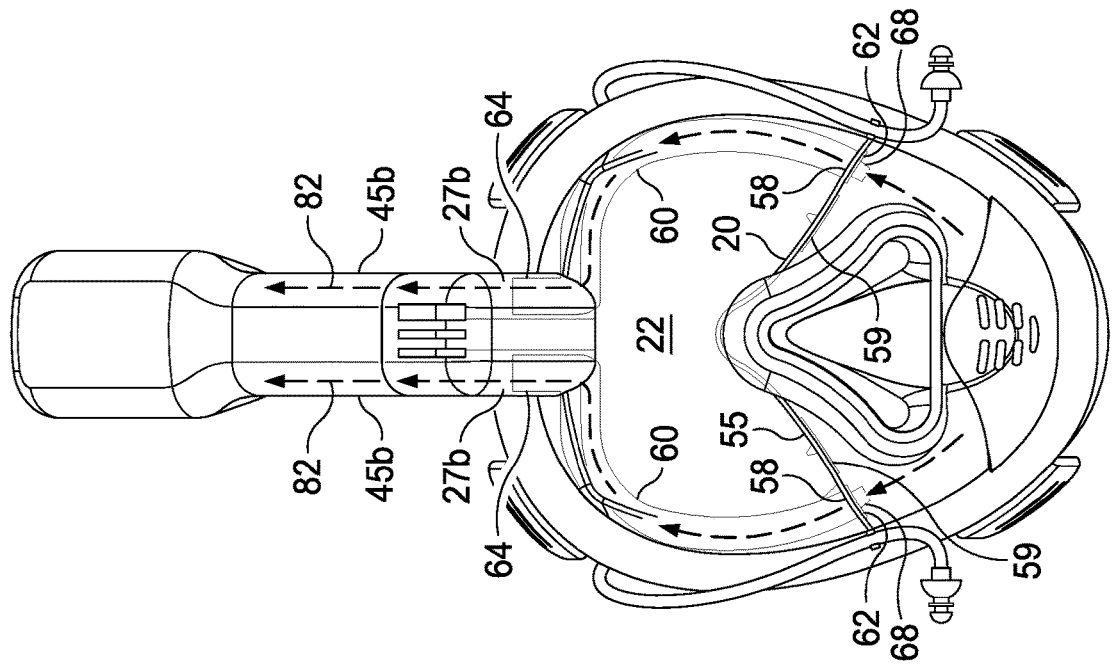
FIG. 7B illustrates the exhale air circuit of the snorkel and diving mask of the present invention.
Figure 7A:
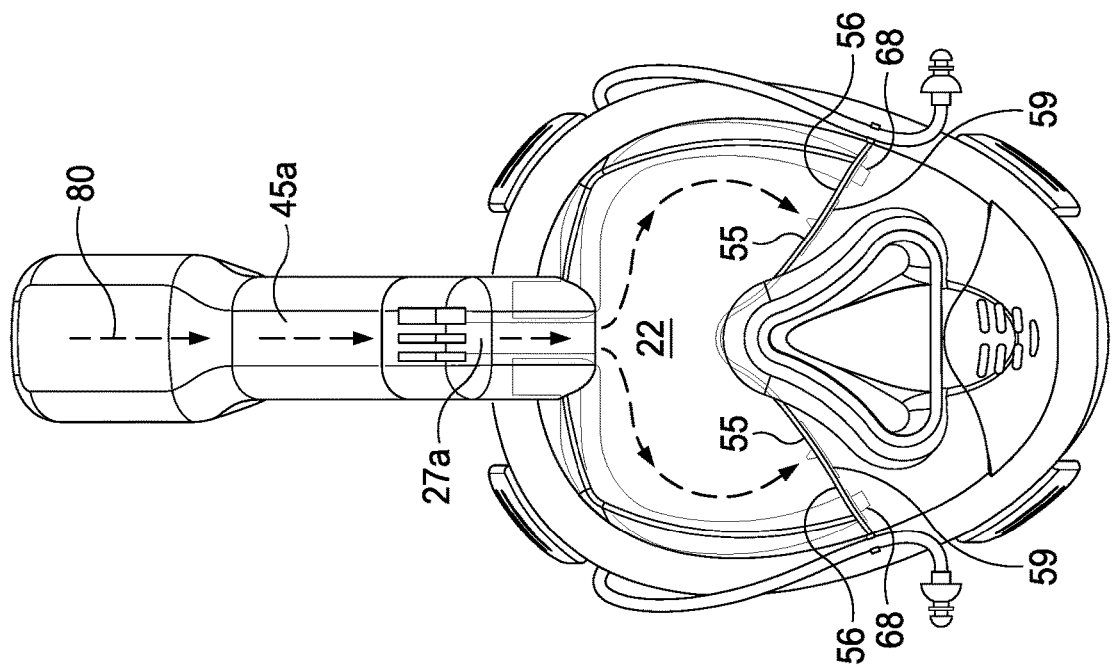
FIG. 7A illustrates the inhale air circuit of the snorkel and diving mask of the present invention.

As shown in FIG. 7A, during the inhalation cycle fresh air 80 enters through the airway inlet 43 near the distal end 46 of the snorkel device 40 device and proceeds through the air passageway 45 to the passageway 27 of the snorkel coupling 26, into the upper chamber 22, through the aperture 55 in the barrier wall section 56 and into the lower chamber 24 of the mask 100. As shown in FIG. 7B, during the exhalation cycle the inlet check valve 59 of aperture 55 automatically seals forcing the exhaled air 82 to proceed up and through the enclosed passageway of the exhaust conduit 60 to the passageway 27 of the snorkel coupling 26, and onto the air passageway 45 of the snorkel device 40 where it exhausts out of the airway inlet 43 near the distal end 46 of the snorkel device 40.

In a preferred embodiment, the snorkel coupling 26 and the snorkel device 40 provides separate pathways or channels for inhaled and exhaled air. For example, with reference to FIGS. 7A and 7B, the air passageway 45 of the snorkel device 40 is divided into inlet 45a and exhaust 45b channels. The inlet 45a and exhaust 45b channels of the snorkel device 40 are properly aligned with corresponding air inlet passageway 27a and the exhaust air passageways 27b formed in the passageway 27 of the snorkel coupling 27 formed in the upper portion 14 of the faceplate 10 of the mask 100. As shown in FIG. 7A, during the inhalation cycle fresh air 80 enters the snorkel device through the airway inlet 43 near the distal end 46 of the snorkel device 40 device and proceeds through the inlet air channel 45a to the inlet passageway 27a of the snorkel coupling 26, into the upper chamber 22, through the aperture 55 in the barrier wall section 56 and into the lower chamber 24 of the mask 100. During the inhalation cycle, the outlet check valve 68 remains closed preventing any exhaust air from the enclosed passageway of the conduit 60 from entering or being inhaled into the lower chamber 24 of the mask 100. As shown in FIG. 7B, during the exhalation cycle the inlet check valve 59 of aperture 55 automatically seals forcing the exhaled air 82 to automatically open the outlet check valve 68 and proceed up and through the enclosed passageway of the exhaust conduit 60 to the exhaust air passageway 27b of the snorkel coupling 26, and into the exhaust air channel 45b formed in the passageway 45 of the snorkel device 40 where it is directed to the airway inlet 43 near the distal end 46 of the snorkel device 40.

The flexible hollow skirt 50 and the flexible insert 8 of the faceplate 10 are preferably made of silicone while the frame 30 and faceplate 10 may be made of rigid plastic such as polypropylene or polycarbonate. The arrangement is advantageous since it allows a mask 100 to be manufactured using a minimum number of parts. Preferably the parts are fused together using injection molding techniques to create a unitary mask body.

The mask 100 of the present invention may also comprise an elastic retention strap 70 which extends between the two or more buckle devices 2 incorporated into the faceplate 10 of the mask 100. In a preferred embodiment shown in FIG. 4, the mask 100 includes two buckle devices 2 extending from the upper portion 14 of the faceplate 10 and two buckle devices 2 extending from the lower portion 16 of the faceplate 10.

In a preferred embodiment, the elastic retention strap 70 may comprise two elastic retention straps bonded together the center of both straps, where each of the straps 70 is attached to a buckles 2 on the same side of the mask and configured on the upper 14 and lower portion 16 of the faceplate 10. For example, a first elastic retention strap 70 having one end attached to a buckle device 2 extending from the upper portion 14 of a first side of the faceplate 10 and a second end attached to a buckle device 2 extending from the lower portion 16 of a first side of the faceplate 10. A second elastic retention strap 70 having one end attached to a buckle device extending from the upper portion of a second side of the faceplate and a second end attached to a buckle device extending from the lower portion of a second side of the faceplate. The configured elastic straps are, therefore, X-shaped making it possible to cover the rear part of the user's head, thereby providing stability while maintaining of the mask snugly on the user's head and face. This preferred embodiment facilitates the mounting operation of the elastic strap and the holding in place thereof in relation to the mask.

Finally, the mask may further include ear buds or earplugs 74 for sealing the user's ears. The earplugs 74 are attached to the mask 100 by means of connecting straps 72 attached to the faceplate 10.

Figure 8:
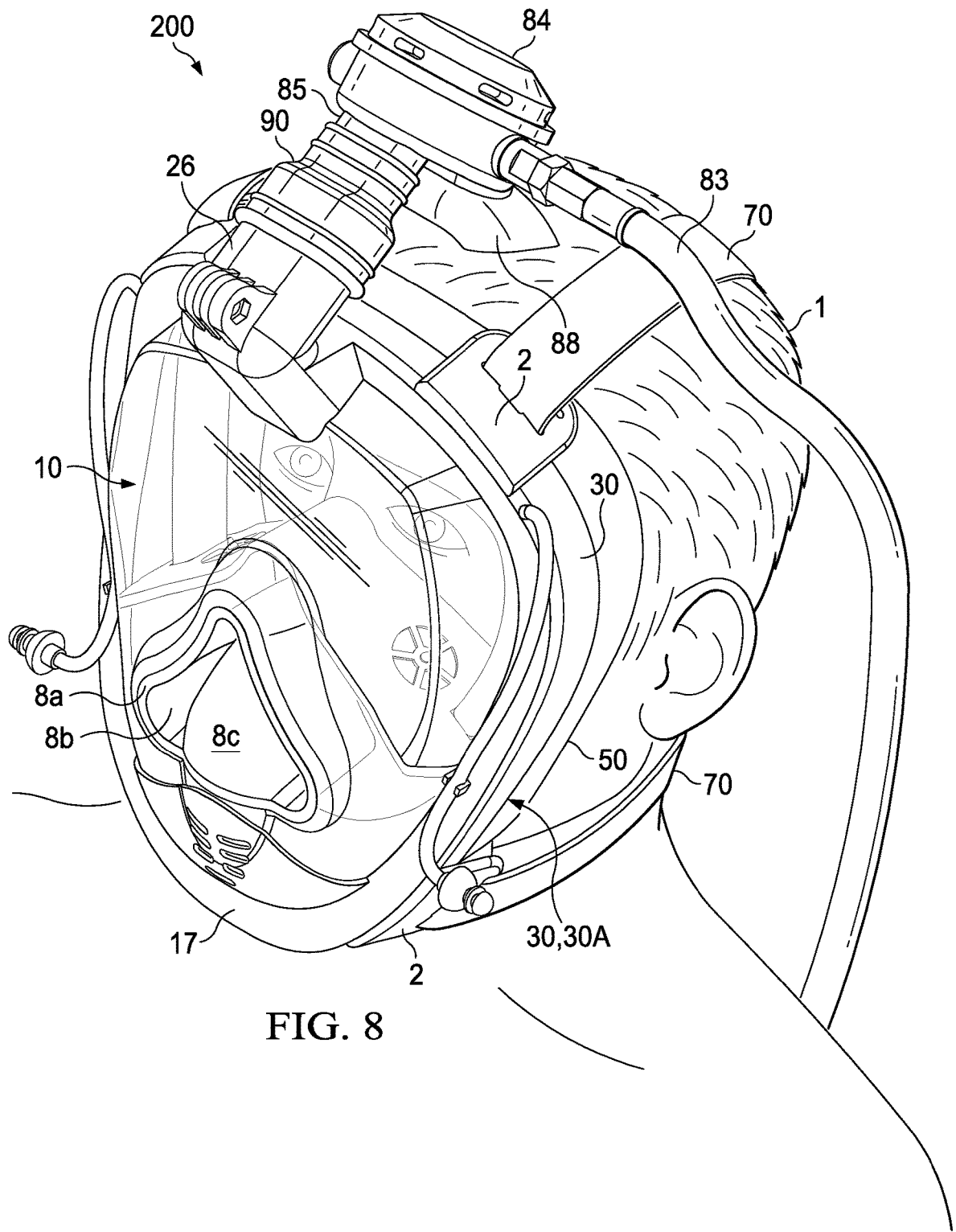
FIG. 8 illustrates a front perspective view of a second embodiment of the snorkel and diving mask of the present invention incorporating a scuba breathing system for underwater diving.
Figure 9:
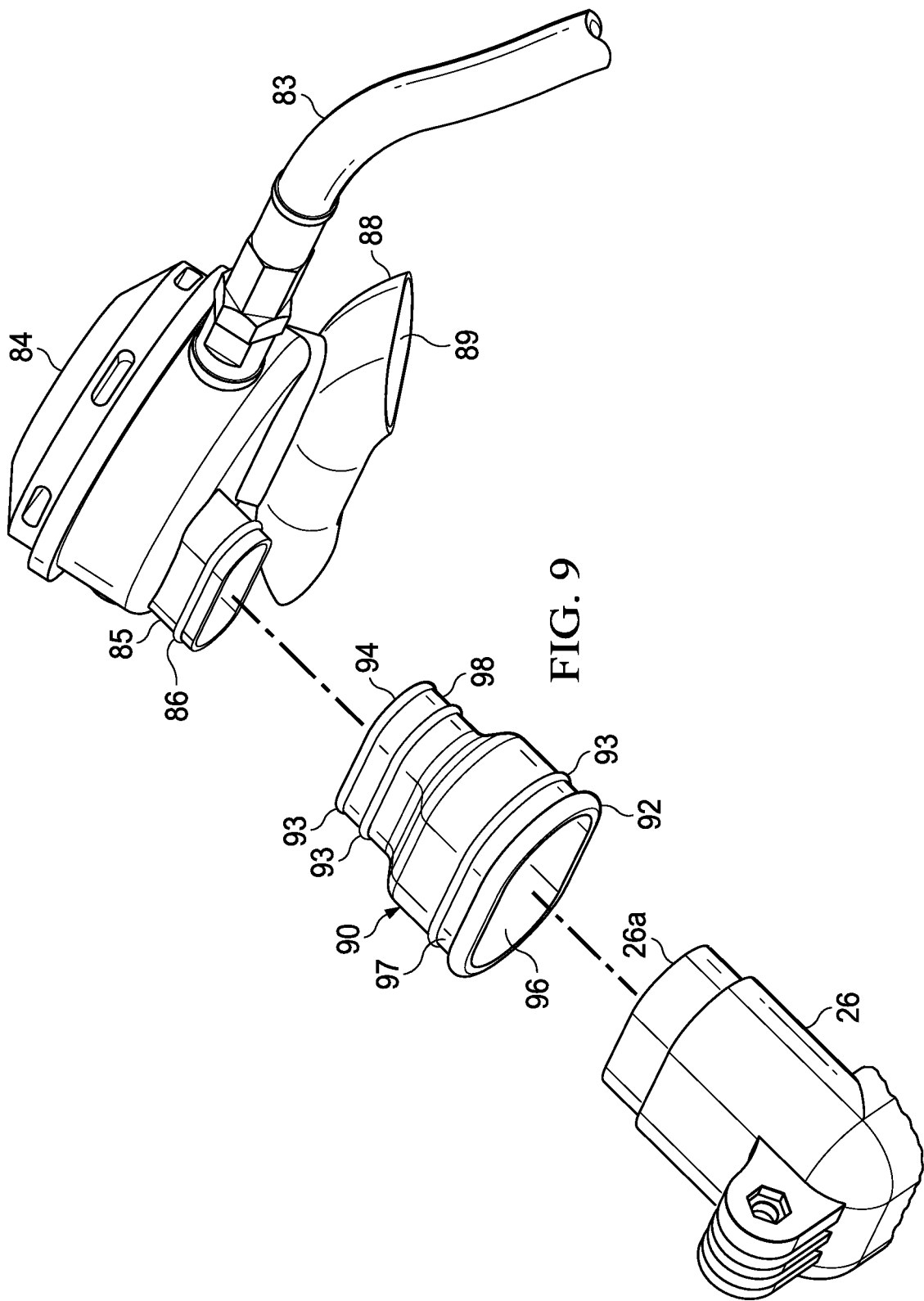
FIG. 9 is an exploded, close-up view of the embodiment of the mask shown in FIG. 8.

With reference now to Figures, and in particular FIGS. 8 and 9, an alternative second embodiment of the diving mask 200 of the present invention is shown which incorporates a conventional $2^{nd}$ stage scuba (i.e., self-contained underwater breathing apparatus) regulator 84. By detaching the snorkel device 40 from the snorkel coupling 26, the mask may be quickly and easily converted into a hybrid scuba mask embodiment 200 by connecting the mouthpiece receiver tube 85 of a conventional $2^{nd}$ stage scuba regulator 84 to the end 26a of the snorkel coupling 26 using a tubular interface sleeve 90. Detaching the snorkel device 40 from the snorkel coupling 26 uncovers the snorkel coupling end 26a and provides access to the passageway 27 contained within the snorkel coupling 26.

The tubular interface sleeve 90 comprises a tubular body 90a that is preferably flexible, yet firm enough to maintain its shape when configured as a passageway between the snorkel coupling 26 and the conventional $2^{nd}$ stage scuba regulator 84. An opened first end 92 of the tubular interface sleeve 90 is dimensioned to fit snuggly onto the outer periphery of the snorkel coupling end 26a while an opposing opened end 94 is dimensioned to fit and seal onto the mouthpiece receiver tube 85 of a conventional $2^{nd}$ stage regulator 84. The tubular interface sleeve 90 forms a watertight connection between the conventional $2^{nd}$ stage scuba regulator 84 and the snorkel coupling 26, and fluidly connects the air inlet 27a and exhaust 27b passageways of the mask 200 with the mouthpiece receiver tube 85 of the regulator 84.

The scuba-enabled embodiment of the mask 200 works essentially the same as previously described snorkel mask 100 (FIG. 1) with a snorkel device attached. However, when a user exhales the exhaust air is directed through the mask, eventually being discharged through the exhaust valve (not shown) in the conventional $2^{nd}$ stage scuba regulator 84. The exhaust air travels up and out of the mask as depicted in FIG. 7B, however, when the exhaust air reaches the end of the exhaust conduits/enclosed passageways 60 of the mask 200 it is directed through the auxiliary passageway 96 of the tubular interface sleeve 90 to the mouthpiece receiver tube 85 of the conventional $2^{nd}$ stage scuba regulator 84, and on to the exhaust valve (not shown) of the scuba regulator 84 where it is preferably vented out of an exhaust tee deflector device 88. Similarly, during an inhalation cycle the user creates a slight vacuum pressure in the air inlet passageways 27a of the mask 200 by breathing in, which triggers the air supply demand valve of the conventional $2^{nd}$ stage scuba regulator 84 to supply pressurized air via air supply hose 83. The air supply hose 83 connects the regulator 84 to a source of pressurized air (e.g., a portable or stationary pressurized canister/tank or a surface air pump). The pressurized air supplied to the scuba regulator 84 flows to the mouthpiece receiver tube 85, through the auxiliary passageway 96 of the tubular interface sleeve 90 and into the air inlet passageways 27a of the mask 200.

A wide variety of conventional $2^{nd}$ stage scuba regulators may be used with the scuba enabled embodiment of the mask. For example, Matsuoka (U.S. Pat. No. 6,718,976) discloses a $2^{nd}$ stage scuba regulator that is suitable for use in the scuba enabled embodiment of the mask 200 in the present invention. The AQUA LUNG® LX model $2^{nd}$ stage regulator has also been successfully utilized with the scuba-enabled embodiment of the mask 200 of the present invention. The exhaust tee deflector device 88 of the AQUA LUNG® LX model regulator advantageously rests on top of the user's head when the regulator 84 is properly attached to the snorkel coupling end 26a of the mask 200 using the flexible elastic tubular interface sleeve 90 as illustrated in FIGS. 8 and 9.

Figure 10A:
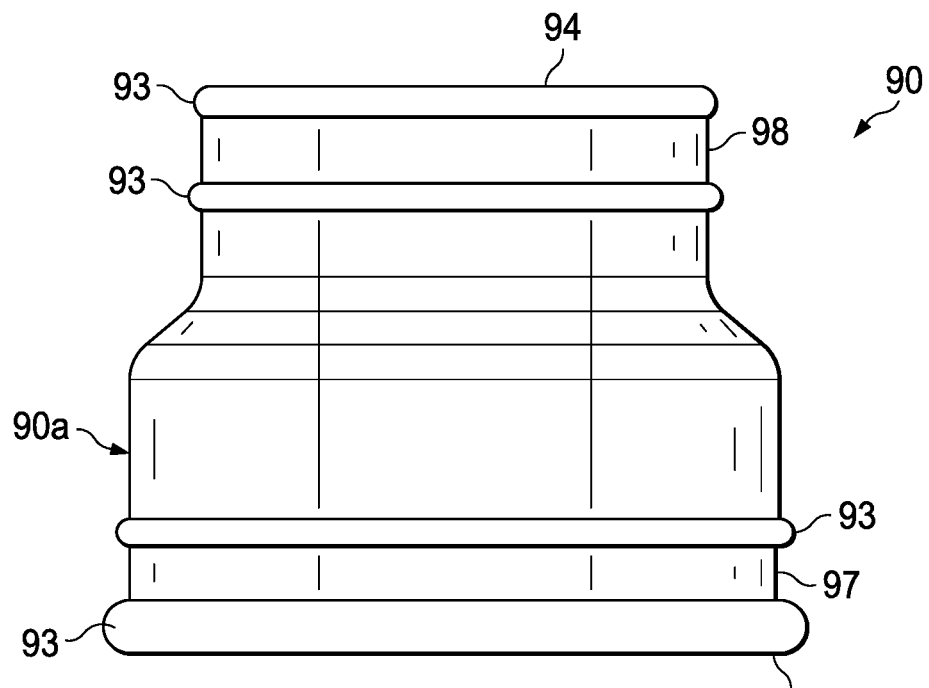
FIG. 10A is a front elevation view of a preferred embodiment of the tubular interface sleeve of the embodiment of the mask shown in FIG. 8.
Figure 10B:
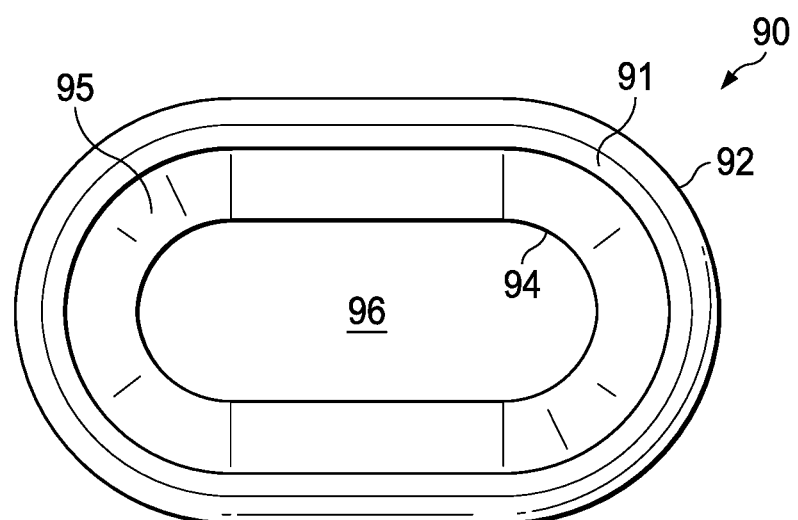
FIG. 10B is an end view of the tubular interface sleeve shown in FIG. 10A.

With reference now to FIGS. 10A and 10B, a preferred embodiment of the tubular interface sleeve 90 is shown. The tubular interface sleeve 90 is preferably made of flexible elastic plastic. The tubular interface sleeve 90 includes a opened first end 92, which is dimensioned to fit snuggly onto the outer periphery of the snorkel coupling end 26a (FIG. 9), and an opposing opened second end 94, which is dimensioned to fit and seal onto the mouthpiece receiver tube 85 (FIG. 9) of a conventional $2^{nd}$ stage regulator 84 (FIG. 9). The interior surface 95 of the tubular interface sleeve 90 defines an auxiliary passageway 96, which extends the entire length of the tubular interface sleeve 90.

While the cross-sectional dimension or area of the auxiliary passageway 96 can be held constant over the length of the tubular interface sleeve 90, it is understood that it may vary over the length of the tubular interface sleeve 90. For example, in the preferred embodiment depicted in FIGS. 10A, 10B the cross-sectional dimension or area of the auxiliary passageway 96 at the first end 92 depicted in the Figures is noticeably larger than the cross-sectional dimension or area of the auxiliary passageway 96 at the second end 94.

In addition, while the opened ends 92, 94 of the tubular interface sleeve 90 are depicted in the drawings as being oblong, it is understood that the opened ends 92, 94 may have any cross-sectional shape that is most conducive to connecting and sealing with a particular snorkel coupling end 26a (FIG. 9) and mouthpiece receiver tube 85 (FIG. 9).

The interior surface 95 of the tubular interface sleeve 90 may include one or more radial projections 91 for securing the seals against the snorkel coupling end 26a (FIG. 9) and the mouthpiece receiver tube 85 (FIG. 9). The interior surface 95 of the tubular interface sleeve 90 may also include a radial groove formed near the opposing opened second end 94 for seating against a flange 86 (FIG. 9) common on many conventional mouthpiece receiver tubes 85.

The tubular interface sleeve 90 may further include first and second exterior radial channel 98, 97 near opposing ends 92, 94 that are bounded by raised rings 93. The exterior radial channels 98, 97 enhance compression attachment by use of a quick-tie or similar radial fastener.

The tubular interface sleeve 90 forms a watertight connection between the conventional $2^{nd}$ stage scuba regulator 84 and the snorkel coupling 26 that fluidly connects the air inlet 27a and exhaust 27b passageways of the mask 200 with the mouthpiece receiver tube 85 of the regulator 84. Fresh air flows from the regulator 84 to the air inlet passageway 27a and into the mask 200 during the inhalation cycle and exhaust air flows up and out of the exhaust conduits/enclosed passageways 60 of the mask and on through the exhaust valve (not shown) of the conventional $2^{nd}$ stage scuba regulator 84 where it is preferably vented out of an exhaust tee deflector device 88 (FIG. 9).

The scuba-enabled embodiment of the mask 200 of the present invention provides a first one-way fluid pathway from the air supply hose 83 (FIG. 9) and regulator 84 (FIG. 9) to the diver's mouth and nasal region during inhalation and a second one-way fluid pathway during exhalation from the diver's mouth and nasal region to the exhaust valve (not shown) of a conventional $2^{nd}$ stage scuba regulator 84 (FIG. 9) where it is preferably vented out of an exhaust tee deflector device 88 (FIG. 9).

Figure 11:
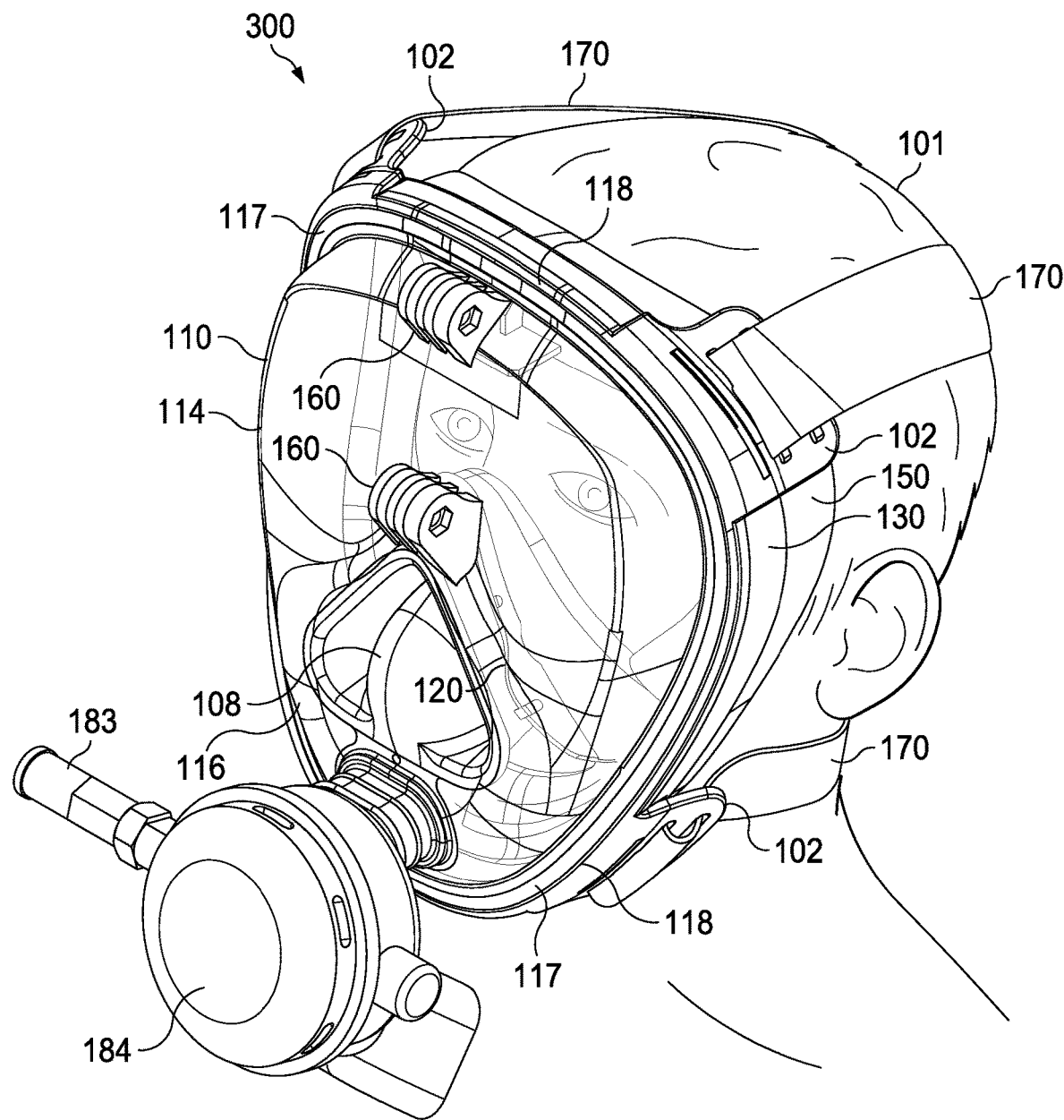
FIG. 11 illustrates a front perspective view of a third embodiment of the diving mask of the present invention incorporating a scuba breathing system for underwater diving.
Figure 12:
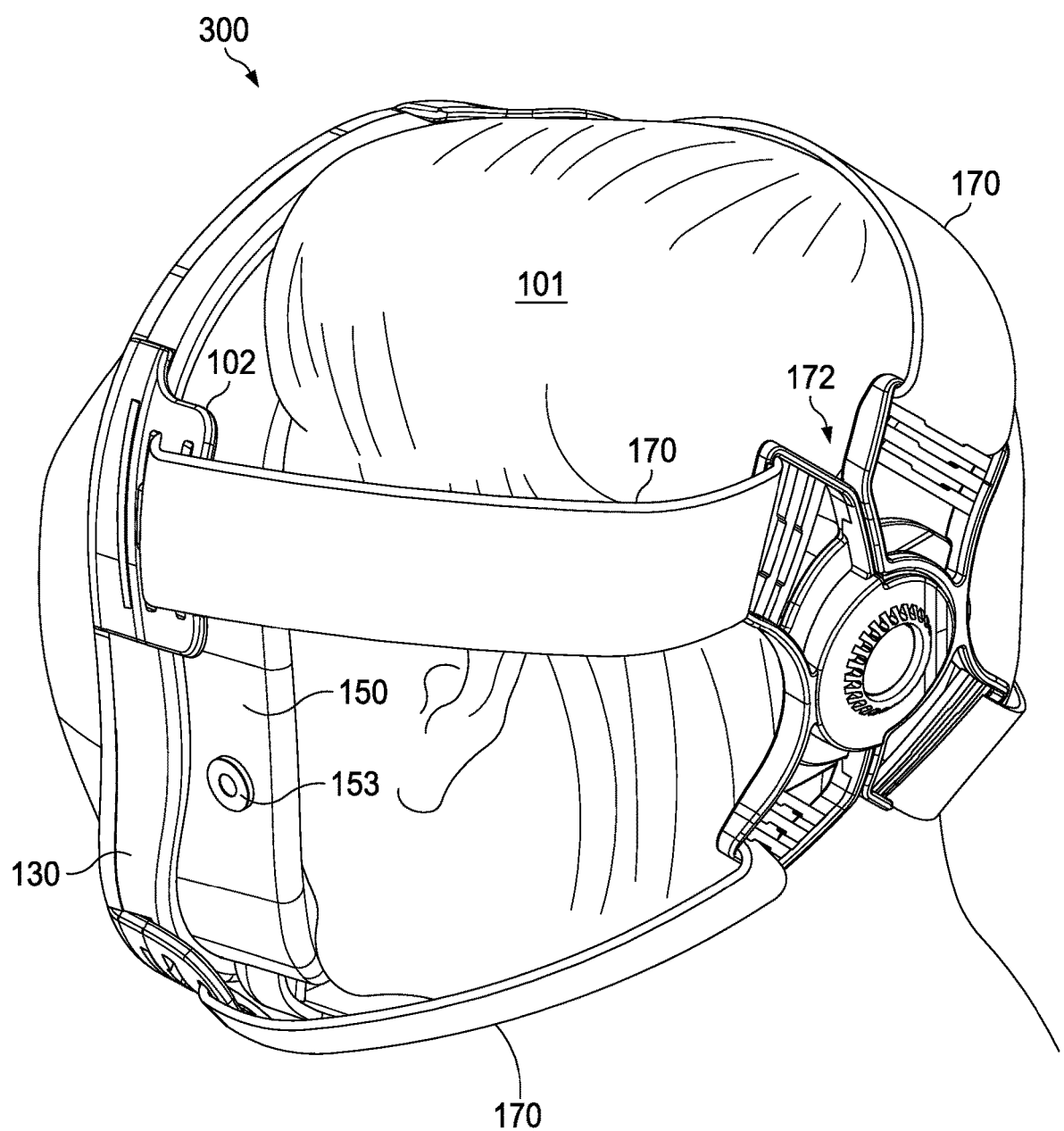
FIG. 12 is a rear perspective view of the third embodiment of the diving mask shown in FIG. 11 illustrating the configuration of the elastic restraining straps' quick-release clasp mechanism on the user's head.
Figure 13:
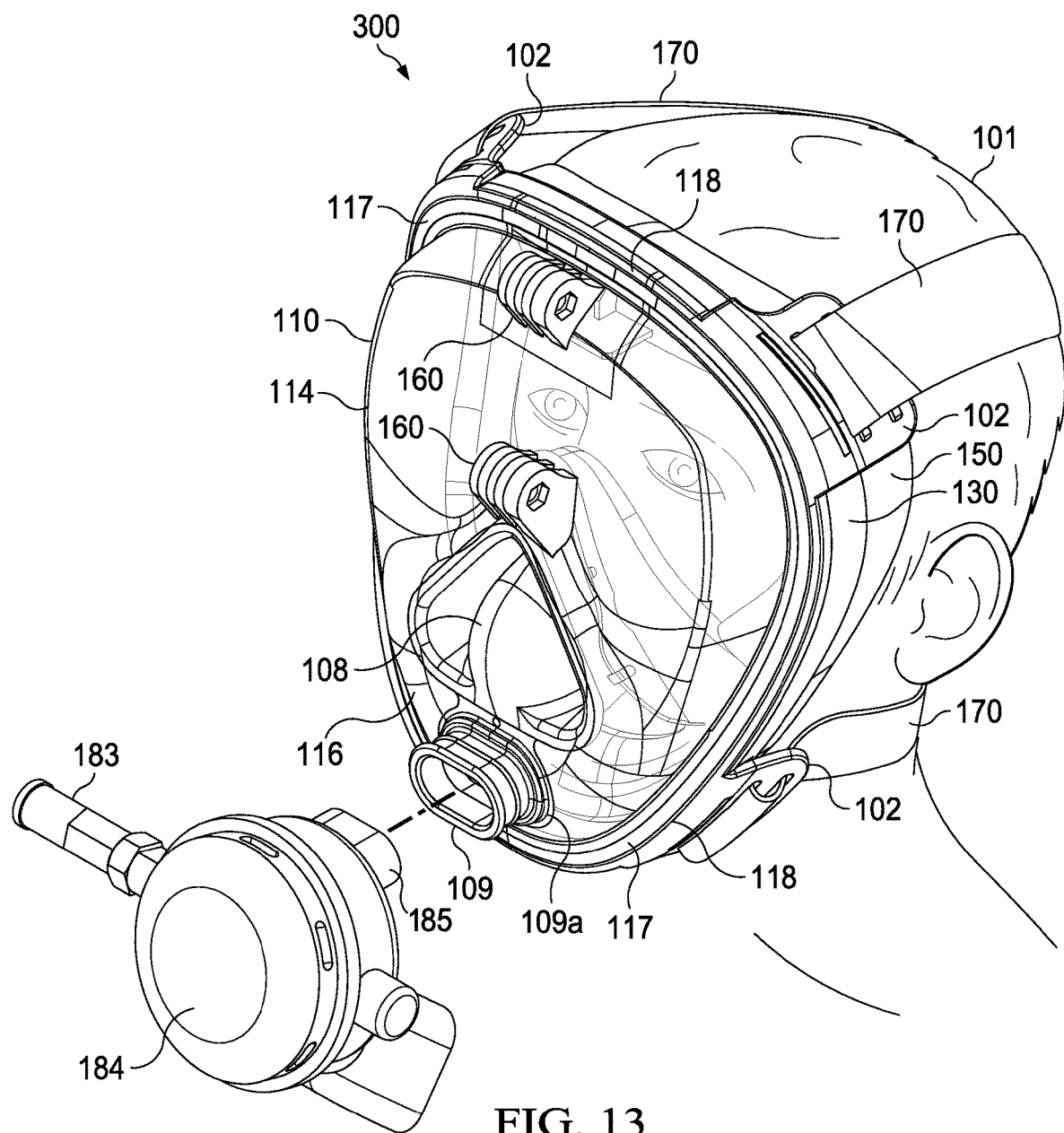
FIG. 13 is a partially exploded, front perspective view of the third embodiment of the diving mask shown in FIG. 11.
Figure 18:
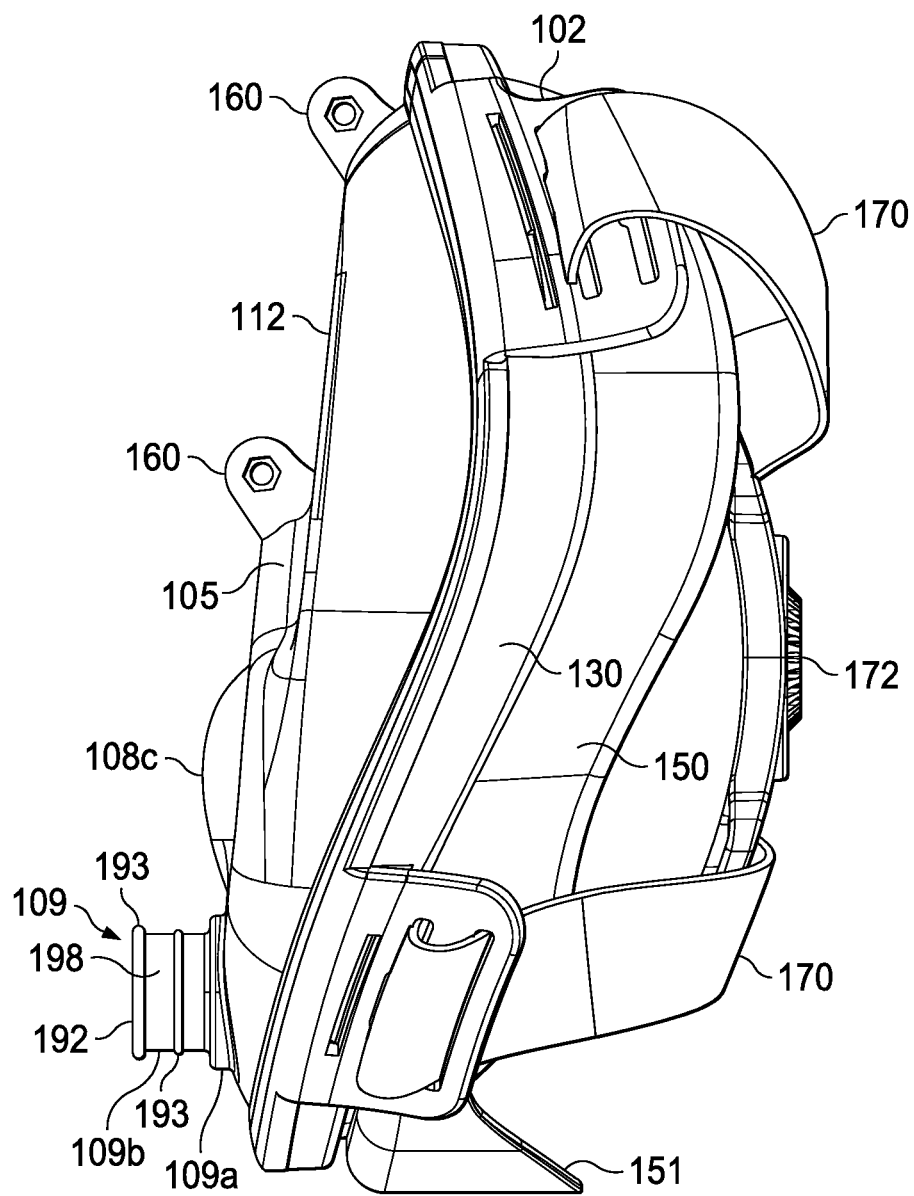
FIG. 18 is a side view of the diving mask in FIG. 11.

With reference now to Figures, and in particular FIGS. 11 and 18, an alternative third embodiment of the diving mask 300 of the present invention is shown, which is specifically adapted to interface and receive a conventional $2^{nd}$ stage scuba (i.e., self-contained underwater breathing apparatus) regulator 184. As with the previously described embodiments, the diving mask 300 comprises a faceplate 110 affixed to or incorporating a rigid annular support rib or frame 130, which in turn is sandwiched between the faceplate 110 and a flexible annular sidewall element or skirt 150.

Figure 16:
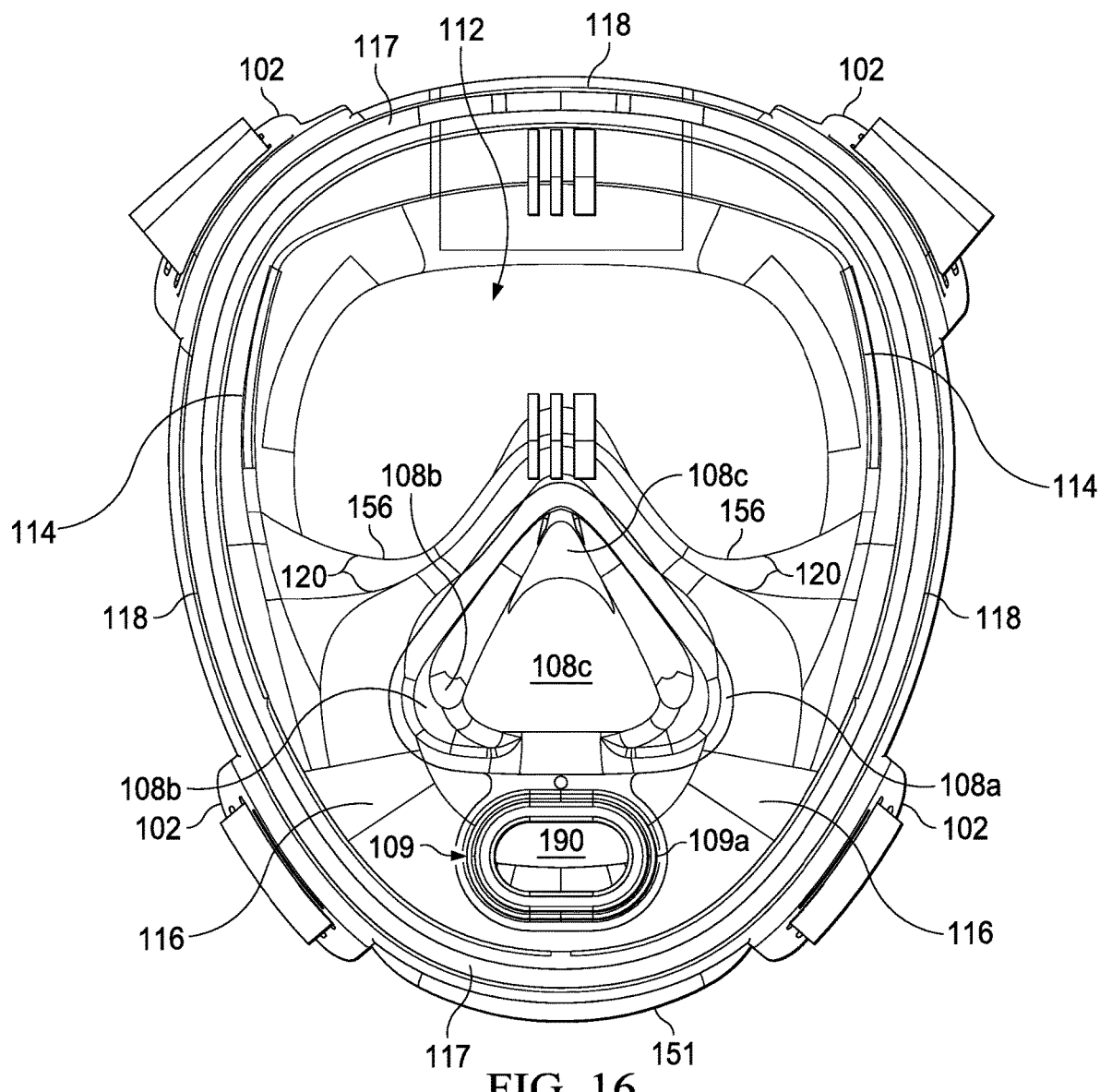
FIG. 16 is a front view of the diving mask in FIG. 11.

The faceplate body 110 includes a lateral partition 120 on the interior side of the faceplate 110 that delineates an upper chamber 122 from a lower or breathing chamber 124. As will be understood with reference to FIG. 16, the user's mouth and nose are positioned in the lower chamber 124, whereas the user's eyes are positioned in the upper chamber 122. The upper portion 114 of the faceplate 110 includes a transparent lens section 112, while the lower portion 116 of the faceplate 110 includes a region 105 that extends away from the transparent lens section 112 and includes two cutouts or openings positioned about the user's mouth and nasal region when worn.

A first or upper cutout 106 is configured about the user's nasal region when worn. A flexible waterproof insert 108 is installed in the first or upper cutout opening 106 that allows the user to readily squeeze the user's nose when necessary to equalized pressure on the eardrums. The insert 108 includes an outer peripheral edge or rim 108a that is complementary to the shape and dimension to the first or upper cutout opening 106 in the faceplate 110. The insert 108 is bonded to the first or upper cutout opening 106 along the outer peripheral edge or rim 108a with a waterproof seal. The insert may also include thin-walled recessed portions 108b and a thin-walled bulbous nose section 108c, which enables a user's to perform the Valsalva maneuver with their hands by grabbing the nose through the thin-walled bulbous nose section 108c. While the preferred embodiment of the first/upper cutout 106 and its corresponding insert 108 shown in the Figures are generally triangular-shaped, it is understood any other conceivable geometric shape may be used.

A second or lower cutout 104 is positioned directly below the first or upper cutout 106 and generally in line with the user's mouth when worn. The second or lower cutout 104 is fitted with a flexible tubular insert 109, which defines a passageway 190 through the faceplate 110 to the lower or breathing chamber 124. The flexible tubular insert 109 includes an outer peripheral edge or rim 109*a* that is complementary to the shape and dimension to the second or lower cutout opening 104 in the faceplate 110. The tubular insert 109 is bonded to the second or lower cutout opening 104 along the outer peripheral edge or rim 109*a* with a waterproof seal. As shown in the Figures, and particularly FIG. 18, the tubular insert 109 extends away from the exterior surface of the faceplate 110 and is dimensioned to fit and seal onto the mouthpiece receiver tube 185 of a conventional $2^{nd}$ stage scuba regulator 184. The distal end of the flexible tubular insert body 109*b* may further include an exterior radial channel 198 formed therein, that is bounded by raised rings 193, The exterior radial channel 198 enhance the compression attachment onto the mouthpiece receiver tube 185 by use of a quick-tie or similar radial fastener.

The flexible tubular insert 109 forms a watertight connection between the conventional $2^{nd}$ stage scuba regulator 184 and the lower or breathing chamber 124 that fluidly connects the lower or breathing chamber 124 of the mask 300 with the mouthpiece receiver tube 185 of the regulator 184. Fresh air flows from the regulator 184 through the tubular insert's passageway 190 and into the lower or breathing chamber 124 of the mask 300 during the inhalation cycle and exhaust air flows out of the lower or breathing chamber 124 of the mask, through the insert's passageway 190 and on through to the exhaust valve (not shown) of the conventional $2^{nd}$ stage scuba regulator 184 where it is preferably vented out of the exhaust tee deflector device.

While the preferred embodiment shown in FIGS. 11 and 18 comprises a generally obround-shaped second/lower cutout opening 104 and flexible tubular insert 109, it is understood any other conceivable geometric shape may be used. Moreover, the distal end 192 (FIG. 18) of the tubular insert 109 may have a geometric shape that is different from the shape of the second/lower cutout opening 106.

While the first 106 and second 104 cutout openings and their complementary inserts are depicted in the Figures as being separate and distinct, it is understood that they may be combined into a single cutout opening configured to receive a complementarily-shaped single insert having both a bulbous nose section and a tubular section defining a passageway through the faceplate 110 to the lower or breathing chamber 124.

Similar to the previously disclosed embodiments, the faceplate 110 of the diving mask 300 of the present invention also includes a flange 117 that is formed along the entire outer periphery or rim 118 of the faceplate 110. The flange 117 is used as a bonding surface to affix the faceplate 110 to a rigid annular oblong-shaped support rib or frame 130 configured within the outer periphery 118 of the flange 117 of the faceplate 110. The rigid annular frame 130 may be bonded or fused to the back side (i.e., the rearward facing side of the flange 117). The rigid annular frame 130 provides structural support to the faceplate 110 while remaining contained within the circumference of the outer periphery 118 of the faceplate 110. Preferably, the rigid annular frame 130 is permanently bonded to the outer periphery flange 117 of the faceplate 110.

As previously noted in regard to the previously described embodiments of the faceplate, in a preferred embodiment a rigid annular rib or frame 130 is incorporated into the faceplate 110 of the diving mask 300 of the present invention as an integral extension formed in the flange 117 of the faceplate 110. The rigid annular support rib or frame 130 is formed in the flange 117 and extends longitudinally away from the backside (i.e., the rearward facing side) of the flange 117 forming a protruding annular lip 130 configured within the outer periphery 118 of the faceplate 110.

With reference again to the Figures, and in particular, FIGS. 11-18, the mask 300 of the present invention also includes a flexible annular sidewall element or skirt 150 that is affixed to the rigid annular frame 130 or the rigid annular lip 130 of the faceplate 110. Similar to previous embodiments, the flexible annular skirt 150 is hollow and filled with a gas or other cushioning substance so as to seal the mask to the diver's face while providing a comfortable, ergonomic and waterproof interface with the diver's face. Preferably, the flexible annular skirt 150 is filled with air or a gel material. The flexible annular skirt 150 has a generally oblong annular shape having substantially the same circumferential dimensions as faceplate 110 and the annular frame 130.

The flexible sealing skirt 150 of the diving mask 300 of the present invention also includes a lateral nose piece section 154 attached to the partition 120 of the faceplate 110. The lateral nose piece section 154 effectively seals off at the partition 120 the upper chamber 122 from the lower chamber 124 when the mask 300 is worn. The lateral nose piece section 154 includes a barrier wall section 56 that is preferably flexible, and fixably attached and bonded to the partition 120. The lateral nose piece 154 is formed or sculpted so as come in sealing contact with the user's face in the nasal region just above the user's nose.

However, in marked contrast to the other previously disclosed embodiments, the barrier wall section 156 of the diving mask 300 of the present invention does not include any openings, apertures or orifices connecting the upper chamber 122 from the lower chamber 124 when the mask 300 is worn. Moreover, the barrier wall section 156 of the diving mask 300 does not include any check valve devices. Consequently, during use the upper chamber 122 is completely sealed off from the lower chamber 124

Figure 14:
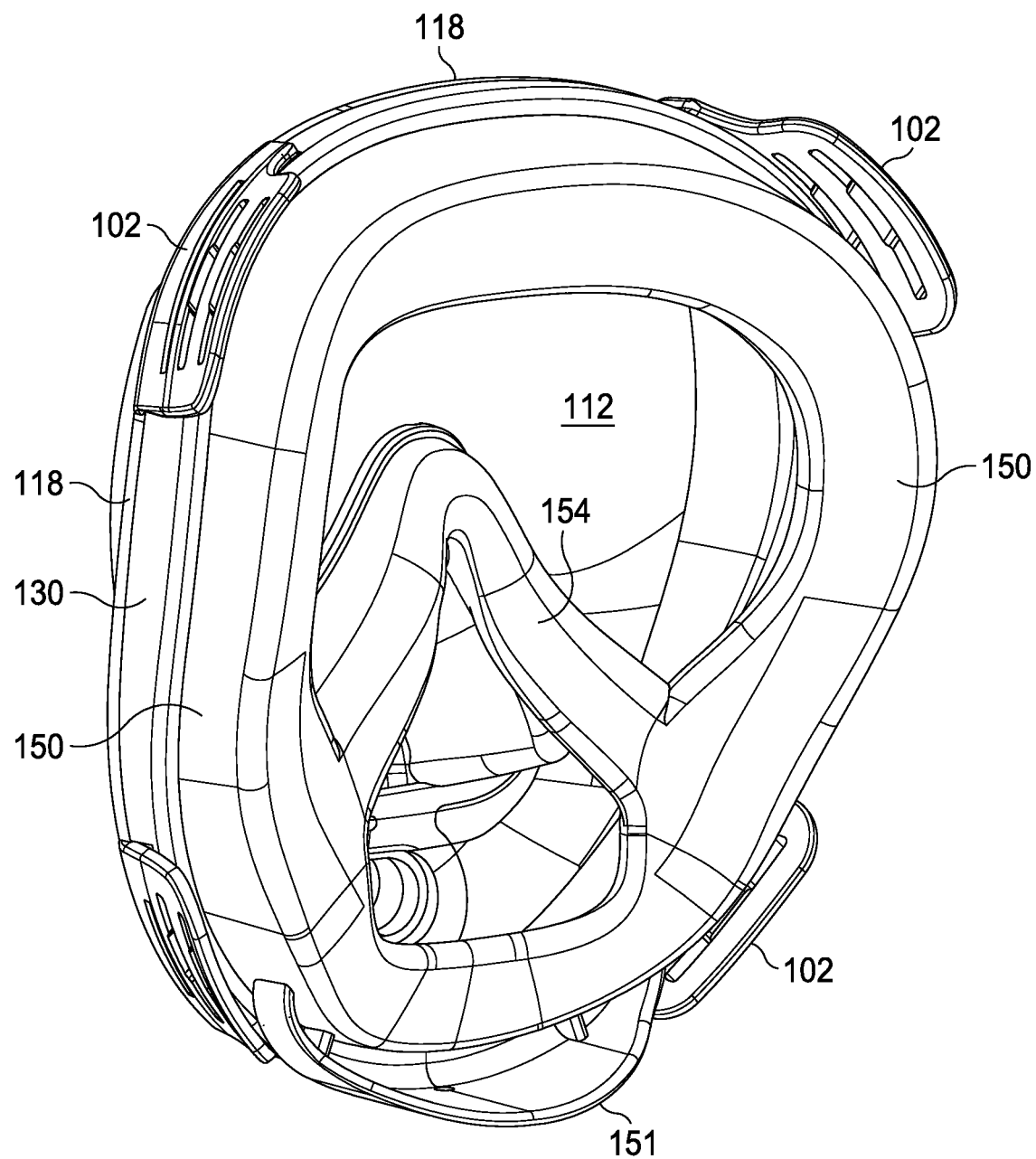
FIG. 14 is a rear perspective view of the diving mask in FIG. 11 with the elastic restraining straps removed.
Figure 15:
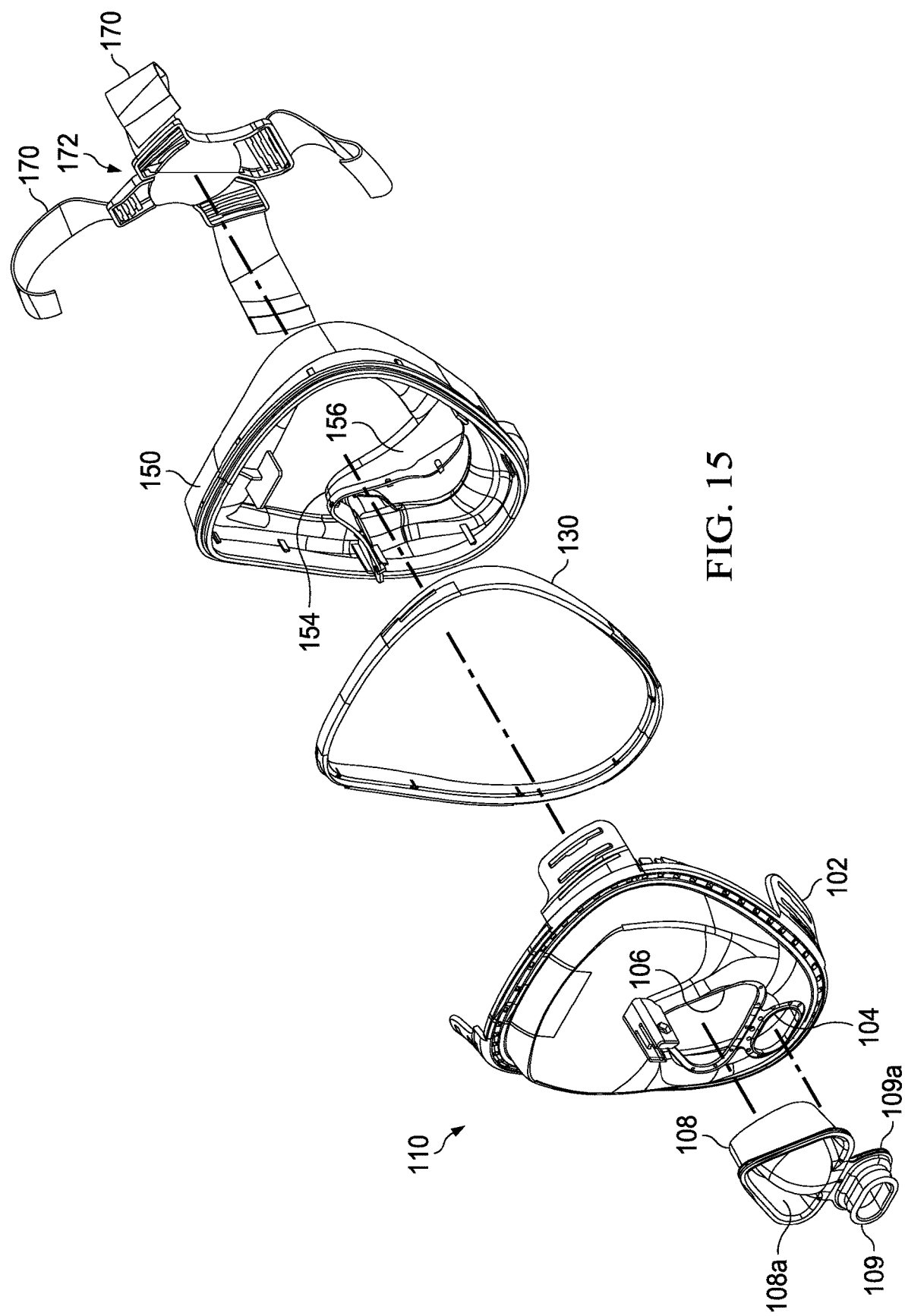
FIG. 15 is an exploded view of the diving mask in FIG. 11.
Figure 17:
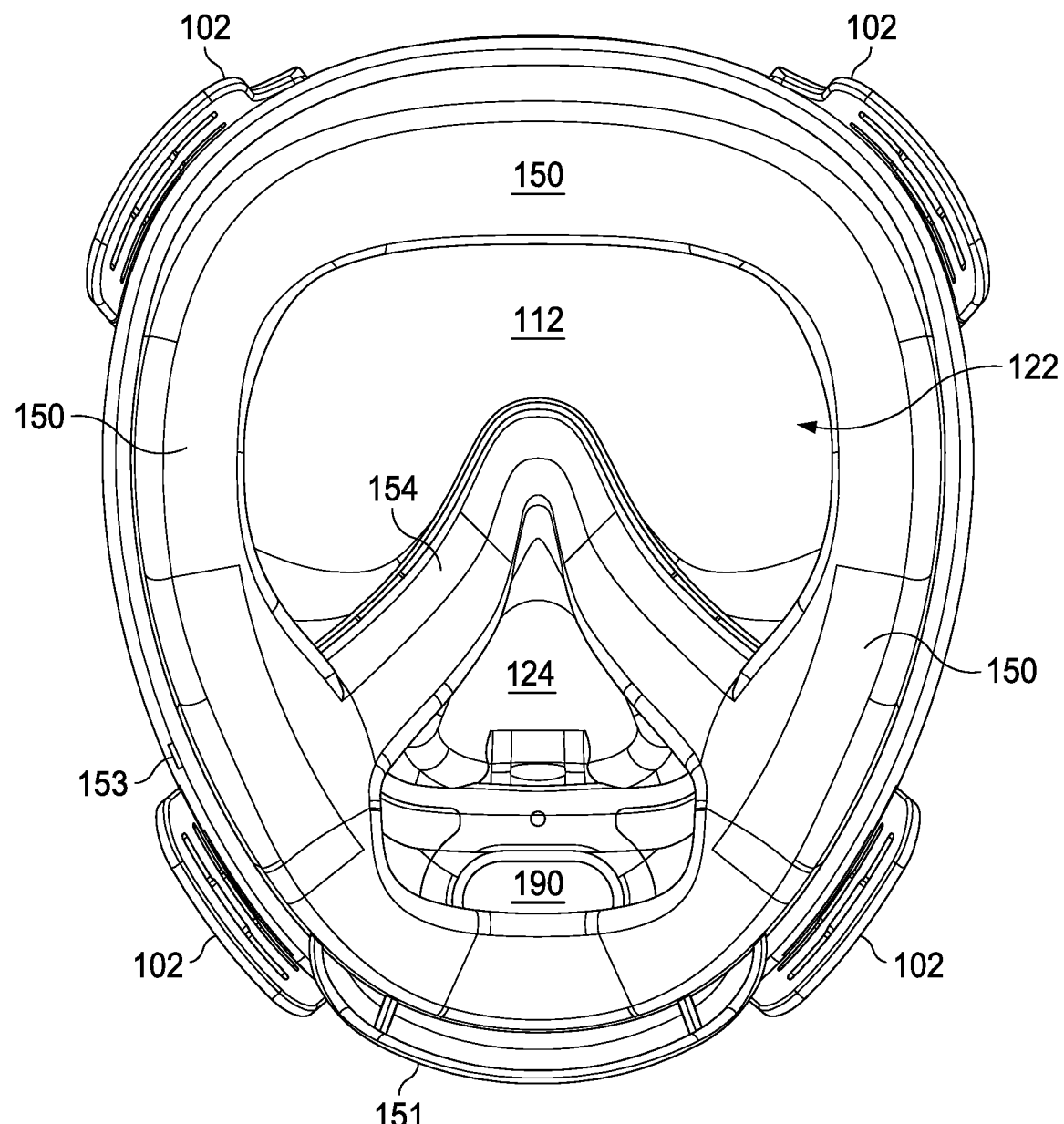
FIG. 17 is a rear view of the diving mask in FIG. 11.

The flexible annular sealing skirt 150 may also include a valve device 153 for varying the amount of cushioning substance in the hollow annular skirt 150. For example, the valve device 153 could be a simple air valve for increasing or decreasing the amount of gas contained in the hollow annular skirt 150. The hollow annular skirt 150 may further include a chin guard 151 configured at the bottom of the mask 300. As depicted in FIGS. 14, 17 and 18, the chin guard 151 extends towards the back of the mask providing protection for the user's chin and assisting in maintaining the proper alignment and positioning of the mask on the user's face.

The faceplate 110 also incorporates two or more, preferably four, buckle devices 102 for attaching an elastic retention strap 170 to the mask. The faceplate 110 may also include one or more accessory mounts 160 formed therein which are used to mount an accessory device, such as a camera, to the mask. For example, as shown in the embodiment of the mask 300 depicted in FIGS. 13, 16 and 18 an accessory mount 160 is configured on the upper portion of the faceplate 110, while another accessory mount 160 is positioned at the transition region 105 that extends away from the transparent lens section 112 in the upper portion 114 of the faceplate 110.

The flexible hollow skirt 150 and flexible inserts (i.e., bulbous nose section insert 108 and the flexible tubular insert 109) are made of a flexible, yet durable material, such as silicone. In contrast, the faceplate 110 and the rigid annular support rib or frame 130, are preferably made of rigid plastic such as polypropylene or polycarbonate. Indeed, the faceplate 110 is preferably formed as a single, unitary body having the rigid annular support rib or frame 130, buckles 102 and accessory mounts 160 formed and incorporated therein. This arrangement is advantageous since it allows a mask 300 to be manufactured using a minimum number of parts. Preferably, the parts are fused together using injection molding techniques to create a unitary mask body.

The mask 300 of the present invention may also comprise one or more elastic retention straps 170, which extend between the two or more buckle devices 102 incorporated into the faceplate 110 of the mask 300. In one embodiment, two elastic retention straps are bonded together in the center of both straps, where each of the straps 170 is attached to a buckles 102 on the same side of the mask and configured on the upper 114 and lower portion 116 of the faceplate 110. For example, a first elastic retention strap 170 having one end attached to a buckle device 102 extending from the upper portion 114 of a first side of the faceplate 110 and a second end attached to a buckle device 102 extending from the lower portion 116 of a first side of the faceplate 110. A second elastic retention strap 170 having one end attached to a buckle device extending from the upper portion of a second side of the faceplate and a second end attached to a buckle device extending from the lower portion of a second side of the faceplate. The configured elastic straps are, therefore, X-shaped making it possible to cover the rear part of the user's head, thereby providing stability while maintaining the mask snugly on the user's head and face.

Alternatively, the elastic retention straps 170 may also include a quick-release clasp mechanism 172 for quickly and easily releasing the retention straps 170 from the user's head. In a preferred embodiment, the quick-release clasp mechanism 172 comprises two component parts 171, 173, which are selectively and easily coupled or latched to one another. The receiver component 171 and clip component 173 each include at least one buckle element 174 for attaching a separate retention strap 170 connected to the mask 300. In a preferred embodiment, the quick-release clasp mechanism 172 includes a centralized quick-release button 177, which quickly decouples and disengages the two component parts from one another when activated.

With reference to the Figures, and particularly FIGS. 11-12 and 18-20, a preferred embodiment of a mask 300 of the present invention is shown depicting the incorporation of the buckle devices 102, retention straps 170 and quick-release clasp mechanism 172. Of course, it is understood that this arrangement could be easily adapted and incorporated into the previously disclosed first 100 and second 200 embodiments of the present invention.

In the preferred embodiment, the mask 300 includes two buckle devices 102 extending from the upper portion 114 of the faceplate 110 and two buckle devices 102 extending from the lower portion 116 of the faceplate 110. A separate elastic retention strap 170 is attached to each buckle device 102. A corresponding distal end of each elastic retention strap 170 is attached to a buckle element 174 on the quick-release clasp mechanism 172.

Figure 19:
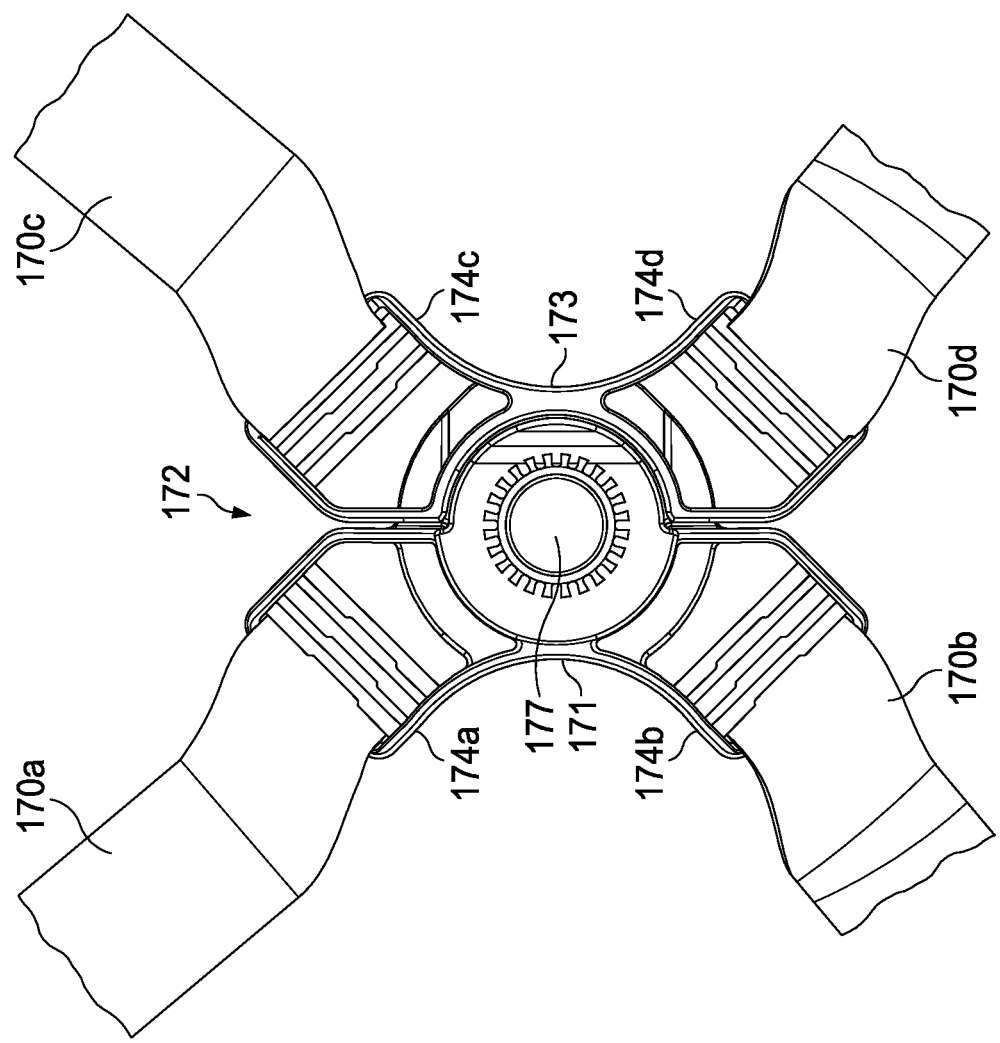
FIG. 19 is a close up view of the quick-release clasp mechanism in the closed or locked position.
Figure 20:
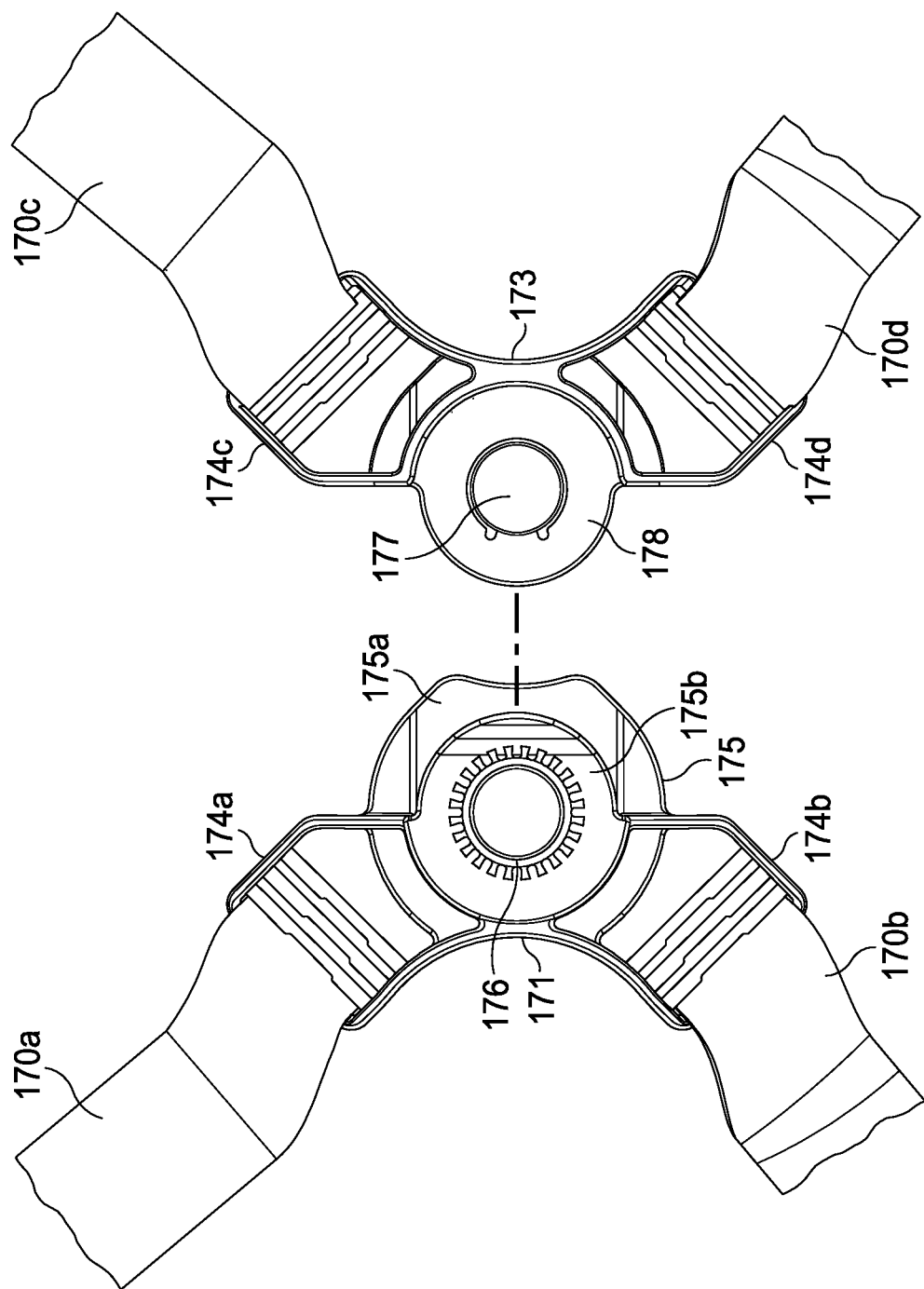
FIG. 20 is a close up view of the quick-release clasp mechanism in the open or unlocked position.

For example as shown in FIGS. 19-20, a first elastic retention strap 170a, which is attached to buckle 102 on the upper left side of the mask 300, is attached to upper buckle element 174a on the left/female/receiver component 171 of the quick-release clasp mechanism 172. Similarly, a second elastic retention strap 17b, which is attached to buckle 102 on the lower left side of the mask 300, is attached to lower buckle element 174b on the left/female/receiver component 171 of the quick-release clasp mechanism 172. In the same way, a third elastic retention strap 170c, which is attached to buckle 102 on the upper right side of the mask 300, is attached to upper buckle element 174c on the right/male/clip component 173 of the quick-release clasp mechanism 172. Finally, a fourth elastic retention strap 170d, which is attached to buckle 102 on the lower right side of the mask 300, is attached to lower buckle element 174d on the right/male/clip component 173 of the quick-release clasp mechanism 172. It is understood that the relative length of each elastic retention strap 170 may be adjusted by the user to customize the snugness of fit of the waterproof interface of the flexible skirt 150 with the user's face.

In the preferred embodiment, the quick-release clasp mechanism 172 comprises a two-piece assembly consisting of a left/female/receiver component 171 selectively coupled to a right/male/clip component 173. By manipulating the quick-release clasp mechanism 172 a user can quickly disengage the latching mechanism coupling the components together. The left/female/receiver component 171 includes a receiver end 175 comprising a lower 175a and upper 175b plate. The upper plate 175b further includes an aperture 176 formed therein. Correspondingly, the right/male/clip component 173 includes an end or tongue section 178 having a shape complementary to the receiver component 171 so as to slide between the lower 175a and upper 175b plates. The end or tongue section 178 of the right/male/clip component 173 further includes a protrusion or button 177 extending away from the surface of the end or tongue section 178 and having a shape that is complementary to the shape of the aperture 176 formed in the upper plate 175b of the receiver end 175 of the left/female/receiver component 171. For example, as depicted in FIG. 20, the aperture 176 and button 177 are round.

The upper plate 175b is capable of flexing in order to receive and capture the button 177 of the end or tongue section 178 within the aperture 176 of the upper plate 175b. To release, a user simply pulls on the upper plate 175b of the of the receiver end 175 causing the upper plate 175b to flex so that the button 177 extending away from the surface of the end or tongue section 178 becomes uncaptured or released from the confines of the aperture 176 of the upper plate 175b. Latent tension forces in the retention strap 170 greatly assist in pulling apart the components of the quick-release clasp mechanism 172 upon the button 177 becoming uncaptured or released from the confines of the aperture 176. Indeed, a user can typically release the clasp mechanism 172 with a single hand.

Alternatively, the button 177 of the end or tongue section 178 may be spring-loaded such that when depressed the end or tongue section 178 can slide between the lower 175a and upper 175b plates of the receiver end 175, and when released or extended the button 177 is captured within the confines of the aperture 176 of the upper plate 175b.

In contrast to the previously described embodiments, the third embodiment of the diving mask 300 of the present invention does not include any openings, apertures or orifices connecting the upper chamber 122 to the lower chamber 124 when the mask 300. Consequently, all breathing operations (i.e., the inhalation and exhalation cycles) are much simpler and contained within the lower chamber 124, the passageway 190 of the flexible tubular insert 109 and a conventional $2^{nd}$ stage scuba regulator 184.

For example, during an inhalation cycle the user creates a slight vacuum pressure in the lower chamber 124 of the mask 300 by breathing in, which triggers the air supply demand valve of the conventional $2^{nd}$ stage scuba regulator 184 to supply pressurized air via air supply hose 183. The air supply hose 183 connects the regulator 184 to a source of pressurized air (e.g., a portable or stationary pressurized canister/tank or a surface air pump). The pressurized air supplied to the $2^{nd}$ stage scuba regulator 184 flows to the mouthpiece receiver tube 185, through the passageway 190 of the flexible tubular insert 109 and into the lower breathing chamber 124 of the mask 300.

During an exhalation cycle, the exhaust air is directed from the lower breathing chamber 124 through the passageway 190 of the flexible tubular insert 109, and into the mouthpiece receiver tube 185 of a conventional $2^{nd}$ scuba regulator 184. The exhaust air then proceeds to an exhaust valve (not shown) in the conventional $2^{nd}$ scuba regulator 184 where it is preferably vented out of an exhaust tee deflector device.

A wide variety of conventional $2^{nd}$ stage scuba regulators may be used with the e third embodiment of the diving mask 300 of the present invention. For example, Matsuoka (U.S. Pat. No. 6,718,976) discloses a $2^{nd}$ stage scuba regulator that is suitable for use in the third embodiment of the mask 300 in the present invention. The AQUA LUNG® LX model $2^{nd}$ stage regulator has also been successfully utilized with the third embodiment of the mask 300 of the present invention.

The third embodiment of the mask 300 in the present invention provides a fluid pathway from the air supply hose 183 (FIGS. 11 & 13) and regulator 184 (FIGS. 11 & 13) to the diver's mouth and nasal region during inhalation and a fluid pathway during exhalation from the diver's mouth and nasal region to the exhaust valve (not shown) of a conventional $2^{nd}$ stage scuba regulator 184 (FIGS. 11 & 13) where it is preferably vented out of an exhaust tee deflector device.

Throughout the description, including the claims, the term "comprising a" should be understood as being synonymous with "comprising at least one" unless otherwise stated. In addition, any range set forth in the description, including the claims should be understood as including its end value(s) unless otherwise stated. Specific values for described elements should be understood to be within accepted manufacturing or industry tolerances known to one of skill in the art, and any use of the terms "substantially" and/or "approximately" and/or "generally" should be understood to mean falling within such accepted tolerances.

It will now be evident to those skilled in the art that there has been described herein an improved snorkel mask. Although the invention hereof has been described by way of a preferred embodiment, it will be evident that other adaptations and modifications can be employed without departing from the spirit and scope thereof. The terms and expressions employed herein have been used as terms of description and not of limitation; and thus, there is no intent of excluding equivalents, but on the contrary it is intended to cover any and all equivalents that may be employed without departing from the spirit and scope of the invention.

I claim:

1. A diving mask comprising: a faceplate having a partition delineating an upper and a lower section, said upper section comprising a transparent lens section and said lower section comprising a purge valve and at least one cutout section having a flexible insert affixed therein, said faceplate having a flange formed along an outer periphery of said faceplate, said upper section having a snorkel coupling defining a passageway through a portion of said transparent lens section to an upper chamber; a rigid annular support frame bonded to a backside of said flange, said frame being configured fully within the outer periphery of said flange: a flexible annular skirt fixed to said rigid annular support frame, the skirt being hollow and filled with a cushioning substance, the skirt comprising a lateral nose piece section attached to the partition and forming the upper chamber and a lower chamber, said lateral nose piece having a barrier wall section defining and sealing off the upper chamber from the lower chamber, said lateral nose piece being arranged for bearing upon the top of a user's nose when the mask is worn by the user so that the user's mouth and nose are located in the lower chamber: wherein the barrier wall section includes at least one aperture arranged to allow the movement of air from the upper chamber to the lower chamber during an inhalation phase, said at least one aperture having a matching inlet check valve that allows the aperture to be open during the inhalation phase and closed during an exhalation phase;

wherein the barrier wall section further includes at least one exhaust orifice containing an exhaust conduit extending from the lower chamber through the upper chamber to the snorkel coupling passageway to allow the movement of exhaled air from the lower chamber through the upper chamber to the snorkel coupling passageway during an exhalation phase, said exhaust conduit having a matching outlet check valve that allows the conduit to be open during the exhalation phase and closed during the inhalation phase.

2. The diving mask of claim 1, wherein said at least one aperture comprises two apertures having matching inlet check valves.

3. The diving mask of claim 1, wherein said at least one exhaust orifice comprises two exhaust orifices having matching exhaust conduits, each exhaust conduit having a matching outlet check valve.

4. The diving mask of claim 1, wherein the outlet check valve is configured near a lower end of the exhaust conduit within the tower chamber of the mask.

5. The diving mask of claim 1, wherein said flexible annular skirt further comprises a valve device for varying the amount of cushioning substance in the hollow annular skirt.

6. The diving mask of claim 1, wherein said faceplate further comprises two or mote buckle devices for attaching an elastic retention strap to the mask.

7. The diving mask of claim 6, wherein the elastic retention strap comprises two elastic retention straps attached to the diving mask and joined with a quick-release clasp mechanism.

8. The diving mask of claim 1, wherein said faceplate and annular support frame are constructed of a rigid plastic.

9. The diving mask of claim 8, wherein said rigid plastic comprises polycarbonate.

10. The diving mask of claim 1, wherein said flexible insert and flexible annular skirt are constructed of silicone.

11. The diving mask of claim 1, wherein said faceplate, frame and flexible annular skirt are fused together using injection molding techniques to form a unitary mask body.

12. A diving mask comprising: a faceplate having a partition delineating an upper and a lower section, said upper section comprising a transparent lens section and said lower section comprising a purge valve and at least one cutout section having a flexible insert affixed therein, said faceplate having a flange formed along the outer periphery of said faceplate, said flange further comprising a protruding annular lip extending longitudinally away from a backside of the flange and configured fully within the an outer periphery of the faceplate, said upper section having a snorkel coupling defining a passageway through a portion of said transparent lens section to an upper chamber; a flexible annular skirt bonded to said annular lip, the skirt being hollow and filled with a cushioning substance, the skirt comprising a lateral nose piece section attached to the partition and forming the upper chamber and a lower chamber, said lateral nose piece having a barrier wall section defining and sealing off the upper chamber from the lower chamber, said lateral nose piece being arranged for bearing upon the top of a user's nose when the mask is worn by the user so that the user's mouth and nose are located in the lower chamber: wherein the barrier wall section includes at least one aperture arranged to allow the movement of air from the upper chamber to the lower chamber during an inhalation phase, said at least one aperture having a matching inlet check valve that allows the aperture to be open during the inhalation phase and closed during an exhalation phase; wherein the barrier wall section further includes at least one exhaust orifice containing an exhaust conduit extending from the lower chamber through the upper chamber to the snorkel coupling passageway to allow the movement of exhaled air from the lower chamber through the upper chamber to the snorkel coupling passageway during an exhalation phase, said exhaust conduit having a matching outlet check valve that allows the conduit to be open during the exhalation phase and closed during the inhalation phase.

13. The diving mask of claim 12, wherein said at least one aperture comprises two apertures having marching inlet check valves.

14. The diving mask of claim 12, whereat said at least one exhaust orifice comprises two exhaust orifices having matching exhaust conduits, each exhaust conduit having a matching outlet check valve.

15. The diving mask of claim 12, wherein the outlet check valve is configured near a lower end of the exhaust conduit within the lower chamber of the diving mask.

16. The diving mask of claim 12, wherein said flexible annular skirt further comprises a valve device for varying the amount of cushioning substance in the hollow annular skirt.

17. The diving mask of claim 12, wherein said faceplate further comprises two or more buckle devices for attaching an elastic retention strap to the diving mask.

18. The diving mask of claim 17, wherein the elastic retention strap comprises two elastic retention straps attached to the diving mask and joined with a quick-release clasp mechanism.

19. The diving mask of claim 12, wherein said faceplate and annular support frame are constructed of a rigid plastic.

20. The diving mask of claim 19, wherein said rigid plastic comprises polycarbonate.

21. The diving mask of claim 20, wherein said flexible insert and flexible annular skirt are constructed of silicone.

22. The diving mask of claim 12, wherein said faceplate and flexible annular skirt are fused together using injection molding techniques to form a unitary mask body.

23. A faceplate fora full-faced diving mask, comprising:
a rigid body having a lateral partition on an interior surface delineating an upper and lower section, said upper section comprising a transparent lens section and said lower section comprising a region that extends away from the transparent lens section anti includes at least one cutout section fitted with a complementary-shaped flexible insert comprising art outer peripheral edge bonded to the cutout section, a thin-walled recessed portion and a thin-walled bulbous nose section that enables a user to grasp the nose and a flexible tubular insert defining a passageway through said faceplate, said tubular insert having a distal end dimensioned to fit and seal onto the mouthpiece receiver tube of a scuba regulator, said faceplate having a flange formed along the outer periphery of said faceplate, said flange further comprising a protruding annular lip extending longitudinally away from a backside of the flange and configured fully within the outer periphery of the faceplate.

24. The faceplate of claim 23, further comprising two or more buckle devices formed in the outer periphery of the faceplate for receiving an elastic retention strap.

25. The faceplate of claim 23, further comprising an accessory mount.

26. The faceplate of claim 25, wherein said accessory mount is configured at a transition area between the transparent lens section and the lower section.

27. The faceplate of claim 23, wherein said as least one cutout section comprises a first cutout section fitted with the complementary-shaped flexible insert, and a second cutout section fitted with the flexible tubular insert.

28. The faceplate of claim 27, wherein said flexible tubular insert includes a tubular body having an exterior radial channel for receiving a radial fastener for enhancing a compression attachment of the tubular insert.

* * * * *